(12) United States Patent
Wilson et al.

(10) Patent No.: US 9,738,940 B2
(45) Date of Patent: Aug. 22, 2017

(54) COMPOSITIONS AND METHODS TO SELECT FOR REDUCED GRAIN MOISTURE IN MAIZE

(71) Applicants: E I DU PONT DE NEMOURS AND COMPANY, Wilmington, DE (US); PIONEER HI-BRED INTERNATIONAL INC, Johnston, IA (US)

(72) Inventors: William Wilson, Noblesville, IN (US); Stuart Gardner, Johnston, IA (US); Jennifer S. Jaqueth, Wilmington, DE (US); Elizabeth S Jones, Raleigh, NC (US); Bailin Li, Hockessin, DE (US)

(73) Assignees: E I DU PONT DE NEMOURS AND COMPANY, Wilmington, DE (US); PIONEER HI-BRED INTERNATIONAL, INC., Johnston, IA (US)

( * ) Notice: Subject to any disclaimer, the term of this patent is extended or adjusted under 35 U.S.C. 154(b) by 332 days.

(21) Appl. No.: 14/379,784

(22) PCT Filed: Feb. 22, 2013

(86) PCT No.: PCT/US2013/027306
§ 371 (c)(1),
(2) Date: Aug. 20, 2014

(87) PCT Pub. No.: WO2013/126689
PCT Pub. Date: Aug. 29, 2013

(65) Prior Publication Data
US 2016/0024598 A1    Jan. 28, 2016

Related U.S. Application Data

(60) Provisional application No. 61/602,188, filed on Feb. 23, 2012.

(51) Int. Cl.
*C12Q 1/68* (2006.01)
*A01H 1/04* (2006.01)
*A01H 5/10* (2006.01)

(52) U.S. Cl.
CPC ............ *C12Q 1/6895* (2013.01); *A01H 1/04* (2013.01); *A01H 5/10* (2013.01); *C12Q 2600/13* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

2005/0138697 A1    6/2005  Wilson

OTHER PUBLICATIONS

Beavis et al., 1994, Crop Science 34: 882-896.*
Maize locus GRMZM2G152908 / ZEAMMB73_713004 (MaizeGDB Gene Record p. 41166).*
Eichten et al., 2011, Plant Physiology 156: 1679-1690.*
David F. Austin et al., Genetic Mapping in Maize with Hybrid Progeny Across Testers and Generations: Grain Yield and Grain Moisture, Crop Science, 2000, pp. 30-39, vol. 40.
W. D. Beavis et al., Identification of Quantitative Trait Loci Using a Small Sample of Toperossed and $F_4$ Progeny from Maize, Crop Science, 1994, pp. 882-896, vol. 34.
G. Blanc et al., Connected populations for detecting quantitative trait loci and testing for epistasis: an application in maize, Theor Appl Genet, 2006, pp. 206-224, vol. 113.
Elisabetta Frascaroli et al., Classical Genetic and Quantitative Trait Loci Analyses of Heterosis in a Maize Hybrid Between Two Elite Inbred Lines, Genetics, May 2007, pp. 625-644, vol. 176.
Martin W. Ganal et al., A Large Maize (*Zea mays* L.) SNP Genotyping Array: Development and Germplasm Genotyping, and Genetic Mapping to Compare with the B73 Reference Genome, PLOS One, Dec. 2011, E28334, pp. 1-15, vol. 6, No. 12.
Elizabeth Jones et al., Development of single nucleotide polymorphism (SNP) markers for use in commercial maize (*Zea mays* L.) germplasm, Mol. Breeding, 2009, pp. 165-176, vol. 24.
H. Lu et al., Genetic basis heterosis explored by simple sequence repeat markers in a random-mated maize population., Theor Appl Genet, 2003, pp. 494-502, vol. 107.
Laurence Moreau et al., Use of trial clustering to study QTL x environment effects for grain yield and related traits in maize, Theor Appl Genet, 2004, pp. 92-105, vol. 110.
Rodrigo G. Sala et al., Quantitative trait loci for grain moisture at harvest and field grain drying rate in maize (*Zea mays*, L.), Theor Appl Genet, 2006, pp. 462-471, vol. 112.
Rodrigo G. Sala et al., Quantitative trait loci associated with grain moisture at harvest for line per se and testcross performance in maize: a meta-analysis, Euphytica, 2012, pp. 429-440, vol. 185.
Chris C. Schon et al., High congruency of QTL for heterosis of grain yield in three crosses of maize, Theor Appl Genet, 2010, pp. 321-332, vol. 120.
International Search Report—PCT/US2013/027306—mailed Sep. 9, 2013.

* cited by examiner

*Primary Examiner* — Amjad Abraham
*Assistant Examiner* — Bratislav Stankovic

(57) ABSTRACT

The invention relates to methods and compositions for identifying and selecting maize plants that have reduced grain moisture. Maize plants generated by the methods of the invention are also a feature of the invention.

2 Claims, 2 Drawing Sheets

US 9,738,940 B2

SEQUENCE LISTING

<160> NUMBER OF SEQ ID NOS: 180

<210> SEQ ID NO 1
<211> LENGTH: 671
<212> TYPE: DNA
<213> ORGANISM: Artificial
<220> FEATURE:
<223> OTHER INFORMATION: PHM18206 reference sequence

<400> SEQUENCE: 1

```
ccaattagaa cgtgatcagc ggcacagggg ctcctagcga cgggtgtaag tcatggagga      60
caagcaacag gaagtccact gccaagtgct tccatcgtcg tcaaatcaca ggtcaggggt     120
taattatatg gggaagaggc cattatcatc aggtacgcgt ggttctcaca cagtcggggc     180
cacgttcgtt gatgatctgc ctcttaatcg gcatctcaaa ctcttgttgt gctctctaca     240
tcagtagaga aggtgtgttg ttcacaagtc gtttcttctt aagactatgt tttggttgat     300
cttgatctat agaactattt tattgtagaa ctactgaacc ctttcgaagt gttgtactca     360
atttgtgtag aacaatgcat gattaatttc taccaatagt ctacggtagc cggtagttgt     420
tttatcctac tagaaattgt tgcatggtta attggttaat ttgtgtagga tgtgccaaaa     480
gaagaggaag agaacaccat caatatgaat ggtgaattat tcgtaagctt atcttccact     540
aatggtgctg gaagccagaa ggagaaagag gaggatggag atcatgtgtc aaggctcagg     600
```

```
agataaatcg aggaagaaaa agatcgaagg gtgtgtttag tgatccttcc agtccaattt    660
tcaaaaacca c                                                         671

<210> SEQ ID NO 2
<211> LENGTH: 468
<212> TYPE: DNA
<213> ORGANISM: Artificial
<220> FEATURE:
<223> OTHER INFORMATION: PHM6567 reference sequence

<400> SEQUENCE: 2
cgctgccccc caattattgg gtgcatgctc agacggaact tggtcatggc tcaaacgttc     60
agggccttga acaactgct acattcgatc caaagactga tgagtttgtc atccacagtc    120
caactctcac gtccagcaaa gtaaagccct atggatcaac tgccaccta ttgatttgtt    180 aaaaacattt gctctttcc ctcttttttc aaaattttct ttagcggttt agccatttgt    240
aatgttaata gttaaagacg ctgccccaaa attcattaca tgtctcttgt tggcagtggt    300
ggcctggtgg cttggggaaa gcttccaccc atgcagtggt gtacgctcgg ttgataactg    360
aaggaaagga ctatggcata catggtagtg ttttgctttt gggaaatgcc tttcttgatg    420
cagtactgtc ttcctttgtg acttatgatg gtcatagctg cctttccc                468

<210> SEQ ID NO 3
<211> LENGTH: 601
<212> TYPE: DNA
<213> ORGANISM: Artificial
<220> FEATURE:
<223> OTHER INFORMATION: PHM4691 reference sequence

<400> SEQUENCE: 3
aaatccragt cagaacgtct ggcgctgcca tcatcgccaa gcgcagggaa tacctgtacc     60
tcggcggtct gctttcatct ggcctctcca ttcttctctg gctgcagttt gctacttcaa    120
tctttggcca caccagcgcg accttcatgt ttgaggtgat gggaacaaat ctgaagctgt    180
aataagaaag catgcaacca agctgactga ctactagctg cagctctact ttggcctcct    240
ggttttcctg ggatatatgg tgtttgacac ccaggagatc atcgagaggg cgcaccgtgg    300
ggacatggac tacatcaagc acgcgctgac tctcttcacc gactttgttt cggttcttgt    360
tcgaatcctt gtcatcatgg tgagtgagtg agtgagtgag tgagtgggca tgctgtctca    420
ggaaatgatt ggtatggttg attccttggt tgattttgca gatgaagaat gcacaggaga    480
aatcccaaga cgagaagaag aggaagaagc ggtagctgct gaattaattg gatgacgtat    540
gttgttgtgg tcactacttc atagtaccgt tactcctatc ctattactat aatttatatt    600
t                                                                    601

<210> SEQ ID NO 4
<211> LENGTH: 399
<212> TYPE: DNA
<213> ORGANISM: Artificial
<220> FEATURE:
<223> OTHER INFORMATION: PHM229 reference sequence

<400> SEQUENCE: 4
agggagtctg atacaatacg gcagtcttgg gttgagcagt gatgtgccta ggggtacggc     60
tcctgctaca aatacagcca gtcttgggtt gagcagtgat gtgcctaggg gaacgactcc    120
tgctacaact acaaccagtc ttgggttgat cagtgattca cctagggtga ttgctcctgc    180
```

```
cagcagtaat tcgcctgggg cgattgcttc tgctacaaat ggtggttccg agatagatgt      240
ggtatgcctg tcagatgatg aatgatgcta gcacgtgtac aaggctgaca gttatagatg      300
actgcttgaa aggactaggc attattttac ggctcccttg agtccgttct gacaaggtgg      360
gaatgttgtt tgtgctgtga atatggtcat agctgttgc                             399

<210> SEQ ID NO 5
<211> LENGTH: 594
<212> TYPE: DNA
<213> ORGANISM: Artificial
<220> FEATURE:
<223> OTHER INFORMATION: PHM9929 reference sequence

<400> SEQUENCE: 5
gtgctccccg ttaggctttt cttgggtgtt gtctggcctc tcttgtcttc aggacgtggc       60
atttgctaga gagctcactg aggccaataa tggtttgtac ctactatctc tctgcctgtg      120
tgtatgaatt acataagcat ttctaaagcc taggataata gcacacgctc atcagtgaga      180
caagcacact aaaaactaac ttaggtttgc aatttatgta atttaaagta tgagtcatac      240
ctgtaaaatg attgtacagt gataaaagct tcttcttgca catgcagagg atgagggaaa      300
gaacatgaaa caaggaggaa tgactgaatt aaaggatgag aaatggggag gtggatataa      360
tggaggatat ggatatggag gtgggtatgg tgatgaatat ggaaaaccgg gctatggtgg      420
tggatatggt gaaggataca ggcccaaata tggcaggggc tacaggtccg gatatggata      480
cggtggcggg tatggtgaag gatacggtgg cggttatggt gggggatatg gtgccgtaat      540
agctattggg aaagtaaagc ttttgaagtt ggcatggtat atccctatcc tggt            594

<210> SEQ ID NO 6
<211> LENGTH: 477
<212> TYPE: DNA
<213> ORGANISM: Artificial
<220> FEATURE:
<223> OTHER INFORMATION: PHM3159 reference sequence

<400> SEQUENCE: 6
acacccamac ctataggaat aggaagtaaa ttgacggagt ttgccagaag gcaatgggca       60
cactgacatc aggattgatg tgaaactcaa caagcacatc tggagcagtg gtatccggag      120
tgtgccgagg cgtgtccgtg tcaggatcgc acgcaagagg aacgatgagg aagacgccaa      180
ggaagagctt tactctcttg ttaccgttgc tgagatcccc ccagaaggcc tgaagggtct      240
gggtaccaag gttgtggagg acgacgagta gatctgcctg ggtactgatc tgtgtcaact      300
gtcaaatcat ttttttggt gttttgagt ttgttagcac taagtcgata gccttgtgag       360
aaatctttga gttttctgat ggcgcgcttg ttctcgtctg gttttgaact tttgaagata      420
cccgcaccaa gtactgtagt ctgtcgttcc aaatctatgg tcatagctgt tcctccc        477

<210> SEQ ID NO 7
<211> LENGTH: 606
<212> TYPE: DNA
<213> ORGANISM: Artificial
<220> FEATURE:
<223> OTHER INFORMATION: PHM15758 reference sequence
<220> FEATURE:
<221> NAME/KEY: misc_feature
<222> LOCATION: (2)..(2)
<223> OTHER INFORMATION: n is a, c, g, or t

<400> SEQUENCE: 7
cnccyttyac cmctgaccat acaaccctct ttcacatgac tgtgagtcga agatcattca       60
```

```
ctgtgacatc aagcctgaga atgttctcct tgacgacaac ttcctcgcga aggtgtcaga    120
cttcggcctc gccaagctga tgaccaggga gcagagccat gtgttcacga cgctcaaggg    180
cactcggggc tatcttgcac ccgaatggat caccaactat gccatctcag agaagtgcga    240
cgtgtacagc tacgggatgg ttctcctcga gataattagt gggaggaaga gctatgatcc    300
tgtggaaggt tcggagaagg ctcacttccc ctcctacgct tttaagaagc tggaagaagg    360
tgacctccgc gatatctccg actccaagct aaaatacaag ggccaggata gccggattga    420
gatggcaatc aaggtcgcct gtggtgcat ccaggaggac ttctatcaga ggccatccat     480
gtccaaggtt gtccagatgc tggaaggcgt gctgcgacgt ccccagccac caatgtcttc    540
gcatattgga taccggctgt acgcgaatgc cttcaaatct agcagcgaat ggttatagct    600
gtttttt                                                              606

<210> SEQ ID NO 8
<211> LENGTH: 704
<212> TYPE: DNA
<213> ORGANISM: Artificial
<220> FEATURE:
<223> OTHER INFORMATION: PHM5208 reference sequence

<400> SEQUENCE: 8
caacaacagg gctgaattgc tggagagtat ggaaaaggct gaaaatgttt gttttggtgg     60
gaatggagtt agtcaaggtg gccttccaga agagttagag gtgatgtttc tggtgcaccc    120
tgctcctgct tttgtgctgt gtaacatgat ctgagtattc tcatttaact ttttctgatg    180
cacaaagcca aaccatagga ttgaagtggt ttcttaagct gatgcaggta tgaacaagga    240
tacatcgtgg aaatcattac tgaggcatgg tcttgaactc agcccttgtg cattcagtat    300
ctgacattgc tctgtttttct ttatactcgg ctgtttggta tttgtctgct actttatggc   360
aggatcagtg gcgtcaacga cacaaaattg aaggaagaat tgtggagata dacaagttct    420
accgcttgct gggtggaatg gtaagtagct caactcacaa gtttccttct ggacacagat    480
ttgcaattgc ggaggtttct ctgacaggag atggtcgaaa atcatgcctt gtaacggcat    540
ggcaaaaaac aacaagaag atttcgtgta agggcatagt cgaatattat gtcttgctgg     600
tacactctag atcagcatgg acttttagtt tttagttttt acttgttgag cagctgcttc    660
ccagagttac ttttttgagt cgatttggtt gagtgactgt wgkt                     704

<210> SEQ ID NO 9
<211> LENGTH: 441
<212> TYPE: DNA
<213> ORGANISM: Artificial
<220> FEATURE:
<223> OTHER INFORMATION: PHM6667 reference sequence

<400> SEQUENCE: 9
aaaaaatggg gaaagtccca gtcacaacga agctggtgc ttcagacgat gaacgtgagg      60
gggatcacca ttgctcatgt aaaaagtcac ttgcaggtaa agcatgttac aaacaggcct    120
acatctcatg actagttagt tgctgtgcta actgagctag ctggtttctt cacataacaa    180 gcgttgggc ctttgatttt tcagatgtac aggagcaaga agctggacca agagtccgct    240
ggacacgaga gagcagcaac ctcctccggt tgtcatctca aatctctctc cccaatttaa    300
ctaaataatc tcctccacag aagcacactg gatgactgga cacacatgca gaaaacgcca    360
tggatcagac tgaatctttt ccttaacctc cgctgctcaa ttttggcagt ttctcgccca    420
```

```
tgactccaac ctttattatt a                                            441
```

<210> SEQ ID NO 10
<211> LENGTH: 511
<212> TYPE: DNA
<213> ORGANISM: Artificial
<220> FEATURE:
<223> OTHER INFORMATION: PHM17246 reference sequence

<400> SEQUENCE: 10

```
aaaggacccc tcttaaggga cggtctggcc cgagctcgag tccgggcaca gggtgaccgg    60
cgcggcggtc tccgccatcg atgcggaggc gatccgtccc ctacctgcag cagagacgac   120
cctgcgggcc ttctcttacg ccccccagga cggcgagcat ggtggcagcg cacttgagtg   180
cgccgtgtgc ctcggcgcgg tcaaggaagg ggagatggtg cggcagctgg cggcctgcat   240
gcatgtgtac cacgtcgagt gcatcgaccg ttggctcgtc gcacaccaca cgtgccccgt   300
gtgccggtcg atcgcagctt gattgattcg ccctaggtac ggtgctgagc ttggatcccc   360
ttctggccgt ccacaccaat aatctgctgc atttcctgtt tggcattgca tctgtagtca   420
ggtaccggta tatcctctta ctaaagtctg taatataata gggaattagg gatgcaagtt   480
gattacgaat ggtcatagcc gtttccgccc c                                  511
```

<210> SEQ ID NO 11
<211> LENGTH: 680
<212> TYPE: DNA
<213> ORGANISM: Artificial
<220> FEATURE:
<223> OTHER INFORMATION: PHM14370 reference sequence

<400> SEQUENCE: 11

```
caaaagcttc caaaccaaag gggagaggac cgtttaaatc caaggtaata tgggtgggtc    60
cgtccccgtc cggccaccat gttcctatga ccttgcatga aaaatccttg cattgcccgg   120
cctcctttg tctgcggctt tatatcaaca acaacaaagg cccaaccatc cacaacaaga   180
ccttcttttt ctctctctgt agtctgtagt cgtcccttc cacatgccta ccccatagga   240
catccggtcc aaaaaccaac ttggctgctc tgctttgcac atttacattg cttacaatac   300
atgctgaacg gcctcctttt ttgccgttgc acagggagaa aaaagctagg acgaggggc   360
gatgtggaag ccactatctt gaggacagaa acagcgtgta taagctattt gcgaggccat   420
tttctagcac acaccagact ttattccttg gttacttgca gaggagatca ggagaaggaa   480
ccaggaaaac tagttcgttc tgagaagatt tatgccagga ggaaaaaggg tggcctgcgc   540
tgcttgggag aactggcgtc tccttctcag tgagaagaga gagctggctt tgttccccct   600
gcgttgacaa gcccgtgctc tagtcctctt ctgatgcgaa ttttagctta cataccaatt   660
gtcattaatt tggaaaaaga                                              680
```

<210> SEQ ID NO 12
<211> LENGTH: 555
<212> TYPE: DNA
<213> ORGANISM: Artificial
<220> FEATURE:
<223> OTHER INFORMATION: PHM6726 reference sequence

<400> SEQUENCE: 12

```
ggaaaatccc agtcacaacg catgagtgca gaatggtctg caagaaaaag actgaaaaag    60
gtgcaacttg agaccttaga aagagtctac ctgcgaagca acggcccac ggtaactcac    120
atttccatca agatcgtcca gactacccaa tagcttatca ttcacttact ttattgcatt   180
```

```
tcatgcagaa tacaatggtc agcagcatag ttcaagtgac aaaccttccg cgaaagacca    240
ttgttaagtg gtttgaggat agaagggagc aagatggagt ccctgaccat cgtgctgcat    300
tcaagagatc cctatctgag attggtgcta gttcataact tcttcagata agcctttgtt    360
acggtgttta cttggaacca ttacaaacat gtaaatttga gctttgaaat tatgacaagt    420
tttgcaagct caacatgcag tatcttttag attgtagtct cagcctatca tgcttatcaa    480
agcggtaaag cgaggagtgg caactaacta ccgccttacg cataagcgag taagcgtaag    540
ataatttttt ataat                                                    555

<210> SEQ ID NO 13
<211> LENGTH: 472
<212> TYPE: DNA
<213> ORGANISM: Artificial
<220> FEATURE:
<223> OTHER INFORMATION: PHM4910 reference sequence

<400> SEQUENCE: 13
ggaggtccca gtcacaacgt atcaaccagc gctcaatgga tgggggcagg gactcggaga     60
tcgccatggg cgcgtaccag ccgtgccacc tgaacaccaa aggccaggtc gcccggggtc    120
aggtccacgg cttccggatg tcgctgtggt acgagcacct cggcatgcta cacgacgatt    180
tcctcaaccc gggaagcctg gagtgtgttc ggagggtaaa ccagatggca gacaggtatt    240
gggacctcta cgctggcgac agcctcgacg ccgacctccc tgggcacctg ctcaggtacc    300
cagtcaccgt cacgaaggag ggcacggtga cagagctccc gggggccaag ttcttccccg    360
acacacaggc gcttgtgctt ggggcgctat cgaagctgcc tcctattctc actacataga    420
gaaaccttct gtactgttgc catgtacgtt gcggctaatt ggtaaattta tt            472

<210> SEQ ID NO 14
<211> LENGTH: 422
<212> TYPE: DNA
<213> ORGANISM: Artificial
<220> FEATURE:
<223> OTHER INFORMATION: PHM4598 reference sequence

<400> SEQUENCE: 14
aaaaaaaaaa aaaaaaaaaa agaagggagg gtcccagtca caacgccact ggtaaaggat     60
ttcgcgagcc ggtataaggc cgcgatcgag ctgatgcact atgatgtgat cacatctttc    120
agcaactttc tttgcgggat ggagatcttg agagcgacgc tcgcacagct cctgctatac    180
tacaccaggc tctccgagtg tgtcaagaga atcaacggcg ctctgctct caacaaggac     240 cttgtctcca tatcctccat cctgttcgaa atcaagaagt attctaggac gttttagttg    300
tttcaccccc ttccatgtac actaggacgg ctagctgagg ggtagctgtg tatccttact    360
ttgtaactgg tatgtgcgac tgcagggaaa caaggcattt gtcggtttat tctgsggttt    420
at                                                                  422

<210> SEQ ID NO 15
<211> LENGTH: 717
<212> TYPE: DNA
<213> ORGANISM: Artificial
<220> FEATURE:
<223> OTHER INFORMATION: PHM3507 reference sequence

<400> SEQUENCE: 15
ggacytattt taaaaacccg atagaatcat gttgatggaa aaacttccag tcatgtttat     60
```

```
tgctttttaa attgtaccga gttttgattg ttgctgggct gctgacccttt tagactacca    120 atcatgagcc ataccatt ttatcatcaa cactaaatgc caacacattg ttagtgccga       180
aaaattaaat atcctgaaga aaatatgcag accatgtctt tccataaact attgaccaaa     240
ttgaaccaaa attcctttag ttctgtcatg ctgcagaatc tgattgggca atgcaaggac     300
acaaattatg attcctcaaa actacagatt catatatgga acaatgttgc aaactaataa     360
ataaataaca ggggaagggt tgggctcact tacctaatcg ctccctggaa cccaaaactt     420
gtttcttgat cctgcttaac tgttggtttt gttgtttatg aatgattgca ggaccgtcct     480
tcaaccaagg tccacgctgc tcctggcggt ggctcttccc tgggctacct gttcggtggc     540
aactgatgcc cgtgctggtg cgctcaccaa agttatcctc ccctgcctgc tgcgtgctat     600
gtctgaatcg tgaacaaccg ttgtcatttc atgtgtgtac cccgtgcaat gcttgtgcgc     660
atggttgatt tctctgtggc aaacttcccg tcctgcatgg gtttaagctt ctcagat       717
```

<210> SEQ ID NO 16
<211> LENGTH: 492
<212> TYPE: DNA
<213> ORGANISM: Artificial
<220> FEATURE:
<223> OTHER INFORMATION: PHM18292 reference sequence

<400> SEQUENCE: 16

```
ggggaaggtc ccagtcacga cgggcatctg ctgagtgatt ctgtaagtac cttcaactat     60
cgatacaaac tttcgttcag tgtatgctgt gggtatttag ctagtgtggt atatataatt    120
ttgcagacgg atccatttaa ccgctcccac ctcactcaag acatgctgat accaaacacg    180
gagctcaagt tgcagatcga ggaatttgtc cagtcccagc agttgagaaa gcgaactgct    240
gcggtgtcag agattggcca agcggatggt gctgatgata tggccgaatg aattgtgcga    300
gcagcaggga tggacatttt cttttgtggt ggggaaagac ggatgctaat ttacgcgaaa    360
tttaccagtt catcggtccg tataaaatcg gtttgccagc ttgtgtcacc atttgtctcc    420
attctttgta aatgttgtaa gtgcacggtt gtaattttaa gtccctgttg ttacctaatt    480
ttgggaaaaa cc                                                        492
```

<210> SEQ ID NO 17
<211> LENGTH: 465
<212> TYPE: DNA
<213> ORGANISM: Artificial
<220> FEATURE:
<223> OTHER INFORMATION: PHM3004 reference sequence

<400> SEQUENCE: 17

```
ggggcaggcc cagtcacaac gatgatgttc cagcagtcag gaacggtagc catgctgctg     60
ccaacgccaa tgggtcatct tccaccagct taccagtacc acacagggtc cacagttcag    120
catccagtag tcgcagagcg gcagaattac aaagcgcatc ctcagcttct tctatgctac    180
taaaagagga aaacgaaata acataggagt tttggagtgt gtagccaggg taaattatat    240
ctgttctctg atccatttcc tcctaggtgt gctgcttcac gctctgcgcc gcagcaaaaa    300
ttgggcactg caagccccca ccattggttt tagtcaagag cgagctcttt cgtttgtgcc    360
cttccaaaag ctgcacaccc tgtttggctg cgcggtgtat gttatgttgt cattaccatt    420
tacgcccatt gtttaaatgc catcagtttt cacttttcgt gttag                    465
```

<210> SEQ ID NO 18
<211> LENGTH: 472

```
<212> TYPE: DNA
<213> ORGANISM: Artificial
<220> FEATURE:
<223> OTHER INFORMATION: PHM14122 reference sequence

<400> SEQUENCE: 18
cgagaacctc attaagaaac cctggggtga ataaaagtcc ggacgatggc atcggtaaag      60
acgaagaaga tcacggccca aatggctcag gggtgcgtat gaatcgtcgt caggagcgtg     120
ccgatgcacg ttacatagaa ctagatgata tgtgatggtg tgttgacccg gatcttgctt     180
ggaaggaggc accagtaggt cattaggtgc acggctacgg taggtagcta gctatagttt     240
acaagaggag gctaaaataa tccacaccca gctgacgtgg tttgcgtgat tcgtttcgtg     300
tgctttgcct gcactgccaa tgccatactg tctgaatctg aaggtgcagg gctactactc     360
actactgagt tactgaccga gcgatgctgc cctcaacgat gtttctgtga ccatcagcgt     420
atcaatcagt ccttgatctg aagcttacat ggtcatagct gttccttccc cc            472

<210> SEQ ID NO 19
<211> LENGTH: 550
<212> TYPE: DNA
<213> ORGANISM: Artificial
<220> FEATURE:
<223> OTHER INFORMATION: PHM10270 reference sequence

<400> SEQUENCE: 19
ggggaggtcc cagtcacgac ggattaccat tgacaagtca tcagaacagg acgctacagc      60
cgcactcctt aaacttaagc agaaggaaca ggtatgcaac agaacaacat gaattaaccc     120
aacccgtgaa agctttgggg agctaacaac gaatggacaa atatttatat caggaagccg     180
aaaagaaggc gaggaagcag ttcaaaggac tctttgacaa gaagccagga gagatatccg     240
aagttggtgt agaatcagat ggtggaaagg atgcaggtga tgcaagaggc aacggtggtg     300
aggcaacgag tgctgataga ggtgtaaaca caaatgacag tccgaccagc gaatcagagt     360
acgccttcga ggaagagagg cccgggcttc ttggcagctt gtggccctct gcgaggatga     420
tcttctcgtc tcttggcatg aacaggtgcg cgatactctg aggtgtccag tttgtactga     480
ggagacatcc aaaatcatgg cagtgaagag aactgccccg agtttctgat taatttcttg     540 ttaattagkt                                                             550

<210> SEQ ID NO 20
<211> LENGTH: 787
<212> TYPE: DNA
<213> ORGANISM: Artificial
<220> FEATURE:
<223> OTHER INFORMATION: PHM14092 reference sequence

<400> SEQUENCE: 20
agtagsctta aaggggacca agtgatgaat tctcattttc aagcttcttc cctttatttt      60
taaggtactg cacatcacaa tcctaaggag atagaagtag gcttaaaggg gaccaagtga     120
tgaattctcg ttttcaagct tcttccctgg attttttaagg tactattttt cacaagtgat     180
cgttgctgta aagtagaggg aaatgcaaat gcaatgcaat aattgtgtga aacaaagaac     240
attttagagt acccccttact cagcaatgtg tgaatcccta gttaaaaaat attagaagaa     300
agttttggat taccattgca attaaacgta acatctaact ctaccttcaa aagcatatat     360
gaagagagag agagagagag ttaggaaaac ggctgtagag ataggtgc tcatccaacc      420 tgtttttcac catgctagcc gtggctcctg gccccaagta aaaacgcaaa aactctagca     480
```

-continued

| | | |
|---|---|---|
| ttaaccctcc aagctccaac tataccaatc attttatgga ttcctagctc tagggttatg | 540 | |
| caaagaactg tccttggatt tttttccct tctctgaaag ttttgctcaa cacttgccga | 600 | |
| ttccaaacaa tacaagactc aacaattcta gaaataaata aaccctaaag tctgttggtt | 660 | |
| ttatttaatt tcataaactt attaaaatgt cgcaggccaa ttttggaccc tattgcttcg | 720 | |
| gtattccaaa aacttttctg tggggcgatt tgcaaaacct gaaggcccag gccaaaaatt | 780 | |
| gggaggg | 787 | |

<210> SEQ ID NO 21
<211> LENGTH: 21
<212> TYPE: DNA
<213> ORGANISM: Artificial
<220> FEATURE:
<223> OTHER INFORMATION: PHM18206 FE primer

<400> SEQUENCE: 21
atatgttcat gttctcactg c    21

<210> SEQ ID NO 22
<211> LENGTH: 20
<212> TYPE: DNA
<213> ORGANISM: Artificial
<220> FEATURE:
<223> OTHER INFORMATION: PHM18206 FI primer

<400> SEQUENCE: 22
tgatcagcgg cacaggtgct    20

<210> SEQ ID NO 23
<211> LENGTH: 21
<212> TYPE: DNA
<213> ORGANISM: Artificial
<220> FEATURE:
<223> OTHER INFORMATION: PHM18206 RI primer

<400> SEQUENCE: 23
ttggaacttg gaaggataca a    21

<210> SEQ ID NO 24
<211> LENGTH: 22
<212> TYPE: DNA
<213> ORGANISM: Artificial
<220> FEATURE:
<223> OTHER INFORMATION: PHM18206 RE primer

<400> SEQUENCE: 24
gaatacttac tagcacactt tc    22

<210> SEQ ID NO 25
<211> LENGTH: 20
<212> TYPE: DNA
<213> ORGANISM: Artificial
<220> FEATURE:
<223> OTHER INFORMATION: PHM6567 FE primer

<400> SEQUENCE: 25
aaaggccaag gaactgagga    20

<210> SEQ ID NO 26
<211> LENGTH: 20
<212> TYPE: DNA
<213> ORGANISM: Artificial
<220> FEATURE:
<223> OTHER INFORMATION: PHM6567 FI primer

```
-continued

<400> SEQUENCE: 26
aataattggg tgctatgctc                                                 20

<210> SEQ ID NO 27
<211> LENGTH: 22
<212> TYPE: DNA
<213> ORGANISM: Artificial
<220> FEATURE:
<223> OTHER INFORMATION: PHM6567 RI primer

<400> SEQUENCE: 27
cataagtcac aaaggaagac ag                                              22

<210> SEQ ID NO 28
<211> LENGTH: 18
<212> TYPE: DNA
<213> ORGANISM: Artificial
<220> FEATURE:
<223> OTHER INFORMATION: PHM6567 RE primer

<400> SEQUENCE: 28
ggtaacccca ggaagtgg                                                   18

<210> SEQ ID NO 29
<211> LENGTH: 20
<212> TYPE: DNA
<213> ORGANISM: Artificial
<220> FEATURE:
<223> OTHER INFORMATION: PHM4691 FE primer

<400> SEQUENCE: 29
gacggcagtt gcttttgcat                                                 20

<210> SEQ ID NO 30
<211> LENGTH: 18
<212> TYPE: DNA
<213> ORGANISM: Artificial
<220> FEATURE:
<223> OTHER INFORMATION: PHM4691 FI primer

<400> SEQUENCE: 30
tctggcgctg ccatcatc                                                   18

<210> SEQ ID NO 31
<211> LENGTH: 22
<212> TYPE: DNA
<213> ORGANISM: Artificial
<220> FEATURE:
<223> OTHER INFORMATION: PHM4691 RI primer

<400> SEQUENCE: 31
tattagtaca ataggatagg ag                                              22

<210> SEQ ID NO 32
<211> LENGTH: 21
<212> TYPE: DNA
<213> ORGANISM: Artificial
<220> FEATURE:
<223> OTHER INFORMATION: PHM4691 RE primer

<400> SEQUENCE: 32
ttcattccca gcagtcatct t                                               21

<210> SEQ ID NO 33
```

-continued

```
<211> LENGTH: 21
<212> TYPE: DNA
<213> ORGANISM: Artificial
<220> FEATURE:
<223> OTHER INFORMATION: PHM229 FE primer

<400> SEQUENCE: 33
aatgcaacaa tgccttccat c                                              21

<210> SEQ ID NO 34
<211> LENGTH: 18
<212> TYPE: DNA
<213> ORGANISM: Artificial
<220> FEATURE:
<223> OTHER INFORMATION: PHM229 FI primer

<400> SEQUENCE: 34
ccctagggca gctcctga                                                  18

<210> SEQ ID NO 35
<211> LENGTH: 22
<212> TYPE: DNA
<213> ORGANISM: Artificial
<220> FEATURE:
<223> OTHER INFORMATION: PHM229 RI primer

<400> SEQUENCE: 35
attcacagca caaacaacat tc                                             22

<210> SEQ ID NO 36
<211> LENGTH: 20
<212> TYPE: DNA
<213> ORGANISM: Artificial
<220> FEATURE:
<223> OTHER INFORMATION: PHM229 RE primer

<400> SEQUENCE: 36
cccagaggtt agcgatttac                                                20

<210> SEQ ID NO 37
<211> LENGTH: 22
<212> TYPE: DNA
<213> ORGANISM: Artificial
<220> FEATURE:
<223> OTHER INFORMATION: PHM9929 FE primer

<400> SEQUENCE: 37
catcagctag aagttcgaaa tg                                             22

<210> SEQ ID NO 38
<211> LENGTH: 21
<212> TYPE: DNA
<213> ORGANISM: Artificial
<220> FEATURE:
<223> OTHER INFORMATION: PHM9929 FI primer

<400> SEQUENCE: 38
tttagtcctt ctcggtgttg t                                              21

<210> SEQ ID NO 39
<211> LENGTH: 22
<212> TYPE: DNA
<213> ORGANISM: Artificial
<220> FEATURE:
<223> OTHER INFORMATION: PHM9929 RI primer

<400> SEQUENCE: 39
```

```
acagtatttc atgcaacata cg                                              22

<210> SEQ ID NO 40
<211> LENGTH: 22
<212> TYPE: DNA
<213> ORGANISM: Artificial
<220> FEATURE:
<223> OTHER INFORMATION: PHM9929 RE primer

<400> SEQUENCE: 40
accatacatg gcatacaaag at                                              22

<210> SEQ ID NO 41
<211> LENGTH: 19
<212> TYPE: DNA
<213> ORGANISM: Artificial
<220> FEATURE:
<223> OTHER INFORMATION: PHM3159 FE primer

<400> SEQUENCE: 41
atggcggaga agaagcagc                                                  19

<210> SEQ ID NO 42
<211> LENGTH: 22
<212> TYPE: DNA
<213> ORGANISM: Artificial
<220> FEATURE:
<223> OTHER INFORMATION: PHM3159 FI primer

<400> SEQUENCE: 42
taaaggaaat caggaagttt gc                                              22

<210> SEQ ID NO 43
<211> LENGTH: 21
<212> TYPE: DNA
<213> ORGANISM: Artificial
<220> FEATURE:
<223> OTHER INFORMATION: PHM3159 RI primer

<400> SEQUENCE: 43
agatttggaa cgacagacta c                                               21

<210> SEQ ID NO 44
<211> LENGTH: 20
<212> TYPE: DNA
<213> ORGANISM: Artificial
<220> FEATURE:
<223> OTHER INFORMATION: PHM3159 RE primer

<400> SEQUENCE: 44
tcgtcagact cagacatgct                                                 20

<210> SEQ ID NO 45
<211> LENGTH: 20
<212> TYPE: DNA
<213> ORGANISM: Artificial
<220> FEATURE:
<223> OTHER INFORMATION: PHM15758 FE primer

<400> SEQUENCE: 45
ttagcatcgc ccttggaaca                                                 20

<210> SEQ ID NO 46
<211> LENGTH: 20
<212> TYPE: DNA
```

```
<213> ORGANISM: Artificial
<220> FEATURE:
<223> OTHER INFORMATION: PHM15758 FI primer

<400> SEQUENCE: 46
tacctccacc atgactgtga                                               20

<210> SEQ ID NO 47
<211> LENGTH: 21
<212> TYPE: DNA
<213> ORGANISM: Artificial
<220> FEATURE:
<223> OTHER INFORMATION: PHM15758 RI primer

<400> SEQUENCE: 47
tcgctgctag atttgaaggc a                                             21

<210> SEQ ID NO 48
<211> LENGTH: 22
<212> TYPE: DNA
<213> ORGANISM: Artificial
<220> FEATURE:
<223> OTHER INFORMATION: PHM15758 RE primer

<400> SEQUENCE: 48
gctaactaaa gcagagcaat gt                                            22

<210> SEQ ID NO 49
<211> LENGTH: 20
<212> TYPE: DNA
<213> ORGANISM: Artificial
<220> FEATURE:
<223> OTHER INFORMATION: PHM5208 FE primer

<400> SEQUENCE: 49
caactttgaa gcgtgtagcg                                               20

<210> SEQ ID NO 50
<211> LENGTH: 21
<212> TYPE: DNA
<213> ORGANISM: Artificial
<220> FEATURE:
<223> OTHER INFORMATION: PHM5208 FI primer

<400> SEQUENCE: 50
gggaacaaca acagtgctga a                                             21

<210> SEQ ID NO 51
<211> LENGTH: 22
<212> TYPE: DNA
<213> ORGANISM: Artificial
<220> FEATURE:
<223> OTHER INFORMATION: PHM5208 RI primer

<400> SEQUENCE: 51
cacagactca aacaagtcaa ct                                            22

<210> SEQ ID NO 52
<211> LENGTH: 20
<212> TYPE: DNA
<213> ORGANISM: Artificial
<220> FEATURE:
<223> OTHER INFORMATION: PHM5208 RE primer

<400> SEQUENCE: 52
agaggtacaa agggccttag                                               20
```

<210> SEQ ID NO 53
<211> LENGTH: 18
<212> TYPE: DNA
<213> ORGANISM: Artificial
<220> FEATURE:
<223> OTHER INFORMATION: PHM6667 FE primer

<400> SEQUENCE: 53
gatggacagg agcaacgc                                                 18

<210> SEQ ID NO 54
<211> LENGTH: 20
<212> TYPE: DNA
<213> ORGANISM: Artificial
<220> FEATURE:
<223> OTHER INFORMATION: PHM6667 FI primer

<400> SEQUENCE: 54
aaagctggtg cttcagacga                                               20

<210> SEQ ID NO 55
<211> LENGTH: 19
<212> TYPE: DNA
<213> ORGANISM: Artificial
<220> FEATURE:
<223> OTHER INFORMATION: PHM6667 RI primer

<400> SEQUENCE: 55
gtggaagtcc atgggcgag                                                19

<210> SEQ ID NO 56
<211> LENGTH: 18
<212> TYPE: DNA
<213> ORGANISM: Artificial
<220> FEATURE:
<223> OTHER INFORMATION: PHM6667 RE primer

<400> SEQUENCE: 56
gtcccctgtc ctcatcat                                                 18

<210> SEQ ID NO 57
<211> LENGTH: 21
<212> TYPE: DNA
<213> ORGANISM: Artificial
<220> FEATURE:
<223> OTHER INFORMATION: PHM17246 FE primer

<400> SEQUENCE: 57
gacagtattc atgctgtgct g                                             21

<210> SEQ ID NO 58
<211> LENGTH: 18
<212> TYPE: DNA
<213> ORGANISM: Artificial
<220> FEATURE:
<223> OTHER INFORMATION: PHM17246 FI primer

<400> SEQUENCE: 58
gagaagggac ggtcctgg                                                 18

<210> SEQ ID NO 59
<211> LENGTH: 21
<212> TYPE: DNA
<213> ORGANISM: Artificial
<220> FEATURE:

<223> OTHER INFORMATION: PHM17246 RI primer

<400> SEQUENCE: 59
tcgtaatcaa cttgcatccc t                                              21

<210> SEQ ID NO 60
<211> LENGTH: 22
<212> TYPE: DNA
<213> ORGANISM: Artificial
<220> FEATURE:
<223> OTHER INFORMATION: PHM17246 RE primer

<400> SEQUENCE: 60
aaagaaccac tcatctagtg tt                                             22

<210> SEQ ID NO 61
<211> LENGTH: 21
<212> TYPE: DNA
<213> ORGANISM: Artificial
<220> FEATURE:
<223> OTHER INFORMATION: PHM14370 FE primer

<400> SEQUENCE: 61
tcctgcttat cacccaacaa g                                              21

<210> SEQ ID NO 62
<211> LENGTH: 18
<212> TYPE: DNA
<213> ORGANISM: Artificial
<220> FEATURE:
<223> OTHER INFORMATION: PHM14370 FI primer

<400> SEQUENCE: 62
ctcctcctgt gaccgcaa                                                  18

<210> SEQ ID NO 63
<211> LENGTH: 22
<212> TYPE: DNA
<213> ORGANISM: Artificial
<220> FEATURE:
<223> OTHER INFORMATION: PHM14370 RI primer

<400> SEQUENCE: 63
acgaatgaac caattggtat gt                                             22

<210> SEQ ID NO 64
<211> LENGTH: 21
<212> TYPE: DNA
<213> ORGANISM: Artificial
<220> FEATURE:
<223> OTHER INFORMATION: PHM14370 RE primer

<400> SEQUENCE: 64
aatggtcaag ctaaatggag c                                              21

<210> SEQ ID NO 65
<211> LENGTH: 22
<212> TYPE: DNA
<213> ORGANISM: Artificial
<220> FEATURE:
<223> OTHER INFORMATION: PHM6726 FE primer

<400> SEQUENCE: 65
cttctaaatc tcaagtgaag ga                                             22

<210> SEQ ID NO 66
<211> LENGTH: 20
<212> TYPE: DNA
<213> ORGANISM: Artificial
<220> FEATURE:
<223> OTHER INFORMATION: PHM6726 FI primer

<400> SEQUENCE: 66
catgagtgca gaatggtctg                                              20

<210> SEQ ID NO 67
<211> LENGTH: 20
<212> TYPE: DNA
<213> ORGANISM: Artificial
<220> FEATURE:
<223> OTHER INFORMATION: PHM6726 RI primer

<400> SEQUENCE: 67
ctcatcttac gccttactcg                                              20

<210> SEQ ID NO 68
<211> LENGTH: 22
<212> TYPE: DNA
<213> ORGANISM: Artificial
<220> FEATURE:
<223> OTHER INFORMATION: PHM6726 RE primer

<400> SEQUENCE: 68
tatgacatgc tcctatacta ct                                           22

<210> SEQ ID NO 69
<211> LENGTH: 20
<212> TYPE: DNA
<213> ORGANISM: Artificial
<220> FEATURE:
<223> OTHER INFORMATION: PHM4910 FE primer

<400> SEQUENCE: 69
cgacgacgaa tacatcatcg                                              20

<210> SEQ ID NO 70
<211> LENGTH: 20
<212> TYPE: DNA
<213> ORGANISM: Artificial
<220> FEATURE:
<223> OTHER INFORMATION: PHM4910 FI primer

<400> SEQUENCE: 70
tatcaaccag cgctcaatgg                                              20

<210> SEQ ID NO 71
<211> LENGTH: 19
<212> TYPE: DNA
<213> ORGANISM: Artificial
<220> FEATURE:
<223> OTHER INFORMATION: PHM4910 RI primer

<400> SEQUENCE: 71
caaccaattc agcccgcaa                                               19

<210> SEQ ID NO 72
<211> LENGTH: 21
<212> TYPE: DNA
<213> ORGANISM: Artificial
<220> FEATURE:
<223> OTHER INFORMATION: PHM4910 RE primer

<400> SEQUENCE: 72
gtagcataat acggagtagc a								21

<210> SEQ ID NO 73
<211> LENGTH: 20
<212> TYPE: DNA
<213> ORGANISM: Artificial
<220> FEATURE:
<223> OTHER INFORMATION: PHM4598 FE primer

<400> SEQUENCE: 73
tgaaggaagc tggaactgag								20

<210> SEQ ID NO 74
<211> LENGTH: 20
<212> TYPE: DNA
<213> ORGANISM: Artificial
<220> FEATURE:
<223> OTHER INFORMATION: PHM4598 FI primer

<400> SEQUENCE: 74
ccactggtaa aggatttcgc								20

<210> SEQ ID NO 75
<211> LENGTH: 22
<212> TYPE: DNA
<213> ORGANISM: Artificial
<220> FEATURE:
<223> OTHER INFORMATION: PHM4598 RI primer

<400> SEQUENCE: 75
acgaagatac aaaccacgac aa							22

<210> SEQ ID NO 76
<211> LENGTH: 22
<212> TYPE: DNA
<213> ORGANISM: Artificial
<220> FEATURE:
<223> OTHER INFORMATION: PHM4598 RE primer

<400> SEQUENCE: 76
agatagaata ggataactgt gg							22

<210> SEQ ID NO 77
<211> LENGTH: 22
<212> TYPE: DNA
<213> ORGANISM: Artificial
<220> FEATURE:
<223> OTHER INFORMATION: PHM3507 FE primer

<400> SEQUENCE: 77
tttcaataat caagatgagc cg							22

<210> SEQ ID NO 78
<211> LENGTH: 20
<212> TYPE: DNA
<213> ORGANISM: Artificial
<220> FEATURE:
<223> OTHER INFORMATION: PHM3507 FI primer

<400> SEQUENCE: 78
atctctttgg aagcggtgag								20

<210> SEQ ID NO 79
<211> LENGTH: 22

```
<212> TYPE: DNA
<213> ORGANISM: Artificial
<220> FEATURE:
<223> OTHER INFORMATION: PHM3507 RI primer

<400> SEQUENCE: 79
aatttagaga cagcttacaa cc                                              22

<210> SEQ ID NO 80
<211> LENGTH: 20
<212> TYPE: DNA
<213> ORGANISM: Artificial
<220> FEATURE:
<223> OTHER INFORMATION: PHM3507 RE primer

<400> SEQUENCE: 80
aaggttcagg cacacgactt                                                 20

<210> SEQ ID NO 81
<211> LENGTH: 20
<212> TYPE: DNA
<213> ORGANISM: Artificial
<220> FEATURE:
<223> OTHER INFORMATION: PHM18292 FE primer

<400> SEQUENCE: 81
ttatcaggca tctgctgagt                                                 20

<210> SEQ ID NO 82
<211> LENGTH: 20
<212> TYPE: DNA
<213> ORGANISM: Artificial
<220> FEATURE:
<223> OTHER INFORMATION: PHM18292 FI primer

<400> SEQUENCE: 82
ggcatctgct gagtgattct                                                 20

<210> SEQ ID NO 83
<211> LENGTH: 21
<212> TYPE: DNA
<213> ORGANISM: Artificial
<220> FEATURE:
<223> OTHER INFORMATION: PHM18292 RI primer

<400> SEQUENCE: 83
caaaggtaaa caaacaggga c                                               21

<210> SEQ ID NO 84
<211> LENGTH: 22
<212> TYPE: DNA
<213> ORGANISM: Artificial
<220> FEATURE:
<223> OTHER INFORMATION: PHM18292 RE primer

<400> SEQUENCE: 84
ctggactata taatcctaga ag                                              22

<210> SEQ ID NO 85
<211> LENGTH: 21
<212> TYPE: DNA
<213> ORGANISM: Artificial
<220> FEATURE:
<223> OTHER INFORMATION: PHM3004 FE primer

<400> SEQUENCE: 85
```
acagcgaagt tgatcttctg g                                              21

<210> SEQ ID NO 86
<211> LENGTH: 21
<212> TYPE: DNA
<213> ORGANISM: Artificial
<220> FEATURE:
<223> OTHER INFORMATION: PHM3004 FI primer

<400> SEQUENCE: 86
atgatgttcc agcagtcagg a                                              21

<210> SEQ ID NO 87
<211> LENGTH: 21
<212> TYPE: DNA
<213> ORGANISM: Artificial
<220> FEATURE:
<223> OTHER INFORMATION: PHM3004 RI primer

<400> SEQUENCE: 87
gggaacgact gatggcattt a                                              21

<210> SEQ ID NO 88
<211> LENGTH: 22
<212> TYPE: DNA
<213> ORGANISM: Artificial
<220> FEATURE:
<223> OTHER INFORMATION: PHM3004 RE primer

<400> SEQUENCE: 88
aatgctgtca tcctatagtt ct                                             22

<210> SEQ ID NO 89
<211> LENGTH: 21
<212> TYPE: DNA
<213> ORGANISM: Artificial
<220> FEATURE:
<223> OTHER INFORMATION: PHM14122 FE primer

<400> SEQUENCE: 89
ggaaatagca tacaacgcca t                                              21

<210> SEQ ID NO 90
<211> LENGTH: 20
<212> TYPE: DNA
<213> ORGANISM: Artificial
<220> FEATURE:
<223> OTHER INFORMATION: PHM14122 FI primer

<400> SEQUENCE: 90
aagagagctc tgggtgacat                                                20

<210> SEQ ID NO 91
<211> LENGTH: 20
<212> TYPE: DNA
<213> ORGANISM: Artificial
<220> FEATURE:
<223> OTHER INFORMATION: PHM14122 RI primer

<400> SEQUENCE: 91
gtaggcttca gatcaaggac                                                20

<210> SEQ ID NO 92
<211> LENGTH: 22
<212> TYPE: DNA
<213> ORGANISM: Artificial

```
<220> FEATURE:
<223> OTHER INFORMATION: PHM14122 RE primer

<400> SEQUENCE: 92
caaatgtact actcaagtcc aa                                              22

<210> SEQ ID NO 93
<211> LENGTH: 22
<212> TYPE: DNA
<213> ORGANISM: Artificial
<220> FEATURE:
<223> OTHER INFORMATION: PHM10270 FE primer

<400> SEQUENCE: 93
ttcaacgatg caaggaatga tt                                              22

<210> SEQ ID NO 94
<211> LENGTH: 21
<212> TYPE: DNA
<213> ORGANISM: Artificial
<220> FEATURE:
<223> OTHER INFORMATION: PHM10270 FI primer

<400> SEQUENCE: 94
gattaccatt gacaagtcat c                                               21

<210> SEQ ID NO 95
<211> LENGTH: 20
<212> TYPE: DNA
<213> ORGANISM: Artificial
<220> FEATURE:
<223> OTHER INFORMATION: PHM10270 RI primer

<400> SEQUENCE: 95
ataaatacca gaaacctcgg                                                 20

<210> SEQ ID NO 96
<211> LENGTH: 22
<212> TYPE: DNA
<213> ORGANISM: Artificial
<220> FEATURE:
<223> OTHER INFORMATION: PHM10270 RE primer

<400> SEQUENCE: 96
tccatacatc caaacttact ct                                              22

<210> SEQ ID NO 97
<211> LENGTH: 20
<212> TYPE: DNA
<213> ORGANISM: Artificial
<220> FEATURE:
<223> OTHER INFORMATION: PHM14092 FE primer

<400> SEQUENCE: 97
tactggtggg catcaagcaa                                                 20

<210> SEQ ID NO 98
<211> LENGTH: 22
<212> TYPE: DNA
<213> ORGANISM: Artificial
<220> FEATURE:
<223> OTHER INFORMATION: PHM14092 FI primer

<400> SEQUENCE: 98
tccaaaggag attagaagta gg                                              22
```

<210> SEQ ID NO 99
<211> LENGTH: 20
<212> TYPE: DNA
<213> ORGANISM: Artificial
<220> FEATURE:
<223> OTHER INFORMATION: PHM14092 RI primer

<400> SEQUENCE: 99
agaagcatca ttctccgcgt                                                  20

<210> SEQ ID NO 100
<211> LENGTH: 20
<212> TYPE: DNA
<213> ORGANISM: Artificial
<220> FEATURE:
<223> OTHER INFORMATION: PHM14092 RE primer

<400> SEQUENCE: 100
cgaattccac cagctgaaag                                                  20

<210> SEQ ID NO 101
<211> LENGTH: 650
<212> TYPE: DNA
<213> ORGANISM: Artificial
<220> FEATURE:
<223> OTHER INFORMATION: PHM10028 reference sequence

<400> SEQUENCE: 101
ggcgcggccc cgttggggga ctaattctca tatatttgca taacttgcat tgttaaatcc       60
tgtcaaacct tgcatatgtt ttctccagtt tccgtatgtt tagcaacgag gacgttacaa      120
ttggatcgtg gatgcttgct atgaacgtca accatgagaa cacacatgcg ctctgtgaac      180
ctgactgcac ggagtcttca gttgctgttt gggacattcc aaaatgctca ggtcattccc      240
tttcttattt cttagattag atcgaaactt gtacattttc ttgccccttg taatgacttg      300
actaacatgc atatttctgt taggatatag ggttacggag gtagtacgag tggtaggttt      360
ggggtccagg accaggacct cgacgcttgg gcgccgtcgg gcggttggat ggggaggcga      420
ggtactgttc aagcggatga acagcgccac gcggatgaac agtgctgttc actgggtggc      480
ctgcgagggt ttgggggcga cggcttgggt taggggcgtt ggggaggtcg gccgcaggga      540
tttccccacg gccaggaaga gagaagggat ttccttctaa tctcttgttt accttcaatt      600
gatacaatct ttctccttat atagaaaggg ttacttgata tctaaccact                 650

<210> SEQ ID NO 102
<211> LENGTH: 669
<212> TYPE: DNA
<213> ORGANISM: Artificial
<220> FEATURE:
<223> OTHER INFORMATION: PHM741 reference sequence

<400> SEQUENCE: 102
tttataagaa ttcaggcaag cttagccttt tgagatttat ttttcagtga ccatttcaat       60
cgactacatt atctggtctt ttaatttcat gtttacttgg ttacagatga ggacaaagac      120
ttggcaaaac tcctcacagg atatcaagat atggttggtt ttttgcatgt ccacaaggtg      180
gcacaaccta acagccaggt cctgaagtat tcacaatcag aacttctgtt taaaaaaaag      240
ctaagtgttc atttgttttg acgccttttta tgttgacaat caggtccctg tgatcttaga      300
ggcatccacg ctctctctaa agctgcgaaa gaggaggtcc ctggtcttag aacggttgaa      360
tcaggctcca gtcgatgggt caagtgggcc ttcgtctgct gcatcaagca gttgctcatc      420

```
gcaaggttca cagcttgatt tctaattggt atggctggtt ttccttgaga ggagctcaga    480
agtgctgtgt actagttact cgtggcaaaa tgcagctttt ggaggtttag gttttagata    540
ggagtcagtt tgatggttca ctgttaacca tcctccctca tgtgtctatc agcttgttgt    600
aaccccactt tcaacatttt agaaccgtcg aaacttgtat attttgggt attttttccaa    660 gttggtgaa                                                            669

<210> SEQ ID NO 103
<211> LENGTH: 554
<212> TYPE: DNA
<213> ORGANISM: Artificial
<220> FEATURE:
<223> OTHER INFORMATION: PHM6289 reference sequence

<400> SEQUENCE: 103
attagcgggg aggtcccagt cacgacgacg accatcaata atctgtcgac tgttgttctt     60
ccaactgctc gtccgtccgc tagcgtcatt ccaatccaac ccaatccatt cgctgggtca    120
gaactgcagc tgcagtaaac gagcattttt ccagtcgaaa tgacccggac ggtacacagc    180
actgggcagc cagcagagat ggtgacgacg ccacgccagc caagcgtctt ccaaatccgt    240
cggcatcgac ggatcccgca tgcatgatac taccccacgt tcaacattac tttctctatt    300 tcttttagt tgtcactaaa tagtacaaaa ttaaattatc taaggacaac taaaaagaaa     360
gagggagtac tcaacagtca acacctgcct ccctccctcc ctccctccat gtgttccgta    420
atccgttccg ttccatgcga taagccacaa ggcgcccgct gaattgccgc atcgcaaacc    480
ggagaaaact gccttgcctc tcgccgcaaa gcaaggctgc agagtcaccg tctgcggctg    540
cgttatgcaa attt                                                      554

<210> SEQ ID NO 104
<211> LENGTH: 600
<212> TYPE: DNA
<213> ORGANISM: Artificial
<220> FEATURE:
<223> OTHER INFORMATION: PHM13089 reference sequence

<400> SEQUENCE: 104
caagcaccaa ctacccggga aaagagcggc taagggcggc cggagcttgc cgcgccggaa     60
gcaggtggcg gcgtcggcgt cggcgtcgga ccaccgcttc caggaaagat cacacaaggt    120
aacgtaactg ttgctgatcc atattctttt tcttcacgga cgaaccgtac gtcgttctaa    180
ttattgatcg ccgctggttg gtttgagcta tgatctccat ctcttgtctc ttgtgtgatg    240
acgcgcaggt gagcaagaag gggcaccagc gagtggagca ggagccgcac aaggaccgat    300
tcgacgccgt cgccgccctg gacgacgacg cttgccagcc tcccacggat tactgagacg    360
acctgctctg tacatagatt tggaaggatt tgcagggcta gctgacgatt tgtttgggct    420
tgcactagtc tgaaagactg cacggttact gtctgctgag tgactgtacg tgtcgtgtcg    480
gtcatgtaaa agttcctcgc tacacgtacg tcgtatcaaa cgtcactcac tgtaaaacgt    540
cacggccaca tacacgatga cgagttccct agacacggca aaatggttat agctggtttt    600

<210> SEQ ID NO 105
<211> LENGTH: 718
<212> TYPE: DNA
<213> ORGANISM: Artificial
<220> FEATURE:
<223> OTHER INFORMATION: PHM2305 reference sequence
```

<400> SEQUENCE: 105

```
gtaaaattgg ggattccaaa tttggccaat ttttcccctg ggggtgatt acctgtaatg      60
tgagtgcctg gtgaataaaa ccatggtaaa cggttgacag gtgaaccaaa tcgggtctgt    120
gaccgagagt atcgaagctg tcaggatgtc caagcgcgcc ggatggggag tgatggcaag    180
ccacaggagg taaacccacc cattgtagtt atttgtccgc tttttgaag acttaacgtt     240
cctatttgat ctgttttgct caattgtcca atcttctctt tattatttgt tcagtggcga    300
gacagaggac accttcattg ctgacctctc agttggcctg tctacggtac gctgtcaact    360
ggtgaagata ctgtcgaatc gaacgtcttg cgtactgaca cctggactcc gtttccatga    420
ctccgtttca gggccaaatc aagacgggag ctccttgccg gtctgagcgc ctggccaaat    480
acaaccaggt aaagcgcgcg caaaccttct tcgtttccca accaggctat gctttacctc    540
tgaaaccaaa cgttcgcggt ttgcagctgc tcaggatcga ggaagagctc ggtgatgccg    600
cggtctacgc cggagcaaag ttcagggcac cagtggagcc ctactaagaa aggaagagga    660
tgaggatgtt ttcttgtgag ctatactagc tcgctgctcc tttacgaaaa aagtgctg     718
```

<210> SEQ ID NO 106
<211> LENGTH: 548
<212> TYPE: DNA
<213> ORGANISM: Artificial
<220> FEATURE:
<223> OTHER INFORMATION: PHM9867 reference sequence

<400> SEQUENCE: 106

```
aaaaaaccc aatccaacag atgagcctcc gtttgacttc ggcgatggcg acacggagct      60
tgaaggcatt ttccggagcg gtgtcgggtg ggagctgctc ccggtgccgc tggacgagga    120
cgagttcgag gtgctgccgg ggcacgtcgt ggaagtgggc ggcgccccgc cggcggcgcg    180
cgcagtggtg gagcggctcc aggtggtggc cgtcagaggc gaggaggttg tgcaggagtg    240
cgctgttgc aaggaaggga tggaacaggg ggagctcacc actgggctgc cgtgtgggca    300
tttctaccac ggggcgtgca ttggtccatg gcttgccatc cggaacacgt gcccggtgtg    360
ccggtatgag ctgcctactg atgaccctga gtatgagaag cggaggacga ggcgccattc    420
tgctggtggt tcaacaccac agttgggtgc accgatgcag gtttgagcta gggctgattg    480
gtgctatgtc ttggatgcaa ttccatcatt ccacggaagt taaaaccctca ctcatacttt    540
ccttaata                                                             548
```

<210> SEQ ID NO 107
<211> LENGTH: 752
<212> TYPE: DNA
<213> ORGANISM: Artificial
<220> FEATURE:
<223> OTHER INFORMATION: PHM7775 reference sequence

<400> SEQUENCE: 107

```
ggaaaaaaat ccaagttatt taaaaaattt ttccttgggg ggcaaratcg taggggaagg      60
ccgtgaagtt cgggttttac tggatcggga tccccaagac ggtcctggtt cctgaggttc    120
aagtgccaaa gtgggttcc gtctatatcc caaccgtaat aacccttctc agtgctgttg     180
ccactccaag gtagtaccaa tcttcccaac aactctatga tcatccagcc atccaaccat    240
caaaaccaac gatgcctttc actctgctct caagctatga taaatccgat gacatttgct    300
tagagatctg acatcaaaac catcggatgg tggtgcaggt cagctcactt agttgtcttc    360
tggaccctct tcgagaatgt gatgtcgctg catagaacca aggccacttt catcggccta    420
```

```
ctggaggcag gcagggtgaa cgagtgggtg gtgacagaaa aactcggtga tgctctcagg      480
accaaagtgc aggcaagaa accccgcatg aggataggag acaggtacac gacgaagaac      540
tgtcttttct gatccatttt ttcttatttt actgggcgaa tgatccatct attccatgat      600
tccatcctcg cggataaact tcgatgtcga atcaggttgc atgttctgga gctcggtgtc      660
gcggcttacc tcctcttctg tggatgctat gacattgcgt tcggaacaac cgctactacg      720
tttaattggg aaaaaaagtt acacgatgac tt                                    752
```

<210> SEQ ID NO 108
<211> LENGTH: 656
<212> TYPE: DNA
<213> ORGANISM: Artificial
<220> FEATURE:
<223> OTHER INFORMATION: PHM16407 reference sequence

<400> SEQUENCE: 108

```
cccgaccttc tcctccccg gagagtcaca tgcactgtac aatatcttcc aatcagccat       60
tctccccatg atacgggttt aataacagat tgtgacccac caattgtaca gttttgttac      120
cccactttgg tgttgtaatt cagttcattg tggcgtcatt ccattacgag gggttgtata      180
cctataaggt tggcacctca gccctaactg attataccttt gcaatacca tatacaaggt      240 gaaatgtatc ggtagttcta ggcgttctct tactgtgttg taacgcccga atgtaattgg      300
gccggttgta ttgtcttgca ggatgacgca taaaaatgct gcagggtctg tcattcagct      360
taaggactat ggagcatctt tttaatattc atttttaccaa tgatgttcat catatatgct      420
gggatcagga agaaagacac gggtatggaa tcatataagc ctatgcatcc atgaaccaca      480
agtcaggtga cctcggcttc tcagagcccc atgttaccat ttgcccattg ccatccccag      540
gatcgtgtta tatatatagc actagagcta caaaccgttt ttgatgttac tactggcttt      600
gctacgtcga ttgttttttaa ttttatacaa aacataaact agagttacat gcatgg         656
```

<210> SEQ ID NO 109
<211> LENGTH: 535
<212> TYPE: DNA
<213> ORGANISM: Artificial
<220> FEATURE:
<223> OTHER INFORMATION: PHM14523 reference sequence

<400> SEQUENCE: 109

```
atatcccagt cacaacgtga ctgagaagca aatgtctact ctttcggtgt tgttttgctt       60
gaggttcttt gtgcaaggcc agtgatcgac cccacgctgc cgagggagat ggtgaacctg      120
gccgagtggg ggatgaagtg gcagaagaga ggagagctgc accagatcat cgatcagagg      180
atctcgggca aatcaggcc ggactctctg aggaagtttg gcgagaccgt ggagaagtgc       240
ctggcagact acggcgtgga gcggccgtcg atgggagacg tcctctggaa cctggagtac      300
gttctgcagc ttcaggacgc cgattcgacg gtctcggatg tgaacagcat gaaccgtatc      360
gtggaactcc cgtcacaggt ccagaacgtc ggggccctcg agagcatcag cgtgacgatg      420
gcagaagccg gagcgtcaaa cgagcctgac cacgacctct ccgatgtgtc catgagccgc      480
gtcttctctc agctgatcaa ggccgaggga gtaaattgct aaattttaa aaaaa            535
```

<210> SEQ ID NO 110
<211> LENGTH: 597
<212> TYPE: DNA
<213> ORGANISM: Artificial
<220> FEATURE:

<223> OTHER INFORMATION: PHM2916 reference sequence

<400> SEQUENCE: 110

```
cggtccccca gtcttgttac attcctcatt catggtgaga gttgactcag agaagcacat    60
cgacttctcg cttaccagcc cacttggtgg tggagaacct ggaagggtga agagaaagaa   120
ccaaaagaag gcttctggtg gaggcggtga cgacgaagag gaagagtgat catgtgatgc   180
tagctccttc gttttgttag ggacctaatt ttgttacatg aaaacaaaaa gttggctgcc   240
gagggttctg aaaaattgca atttaaaatt ttgagaactg taattgctaa gactcttcat   300
tgccgaagtt gtttatccga tgaacacatg ttaattcagt gagcttgcac tgctgcctac   360
atgagatcac tttctgtcag gaagatatta gtgagcttgc attgccgaag ttgtttatcc   420
gatgaacatg ttaattcagt gagctatgca ctgctgctta catgagatca ctttctgtca   480
ggaagatatt agtgtgtact ccgatatata gatctgggat atgtttcgaa gtatttatt    540
tatatatagc tacgcactcg acatgtggta ttcttaaggg tcaaaggggc cttgggg      597
```

<210> SEQ ID NO 111
<211> LENGTH: 512
<212> TYPE: DNA
<213> ORGANISM: Artificial
<220> FEATURE:
<223> OTHER INFORMATION: PHM4583 reference sequence

<400> SEQUENCE: 111

```
agaggttcaa agcaggaaat gcggttcact tagctttttt atcaaaaaat gttggaggtt    60
ccaagtcaaa agtttctttc aagtagatga ctgttttggc cacccgcagt gggttgtcca   120
taccatgtcc tgaaggaagc aaagtgcggt tggcccagct tagtggggat atcagcagcc   180
ctccctgaa gggcgaattc cttttgctgt tttaacccat gtttgttagg cctttattc     240
cagaaaccta tgcaaaactc tgctataagt ttgccaagaa atgctaactg cagttgttat   300
gttttcagca atttcagggt aagaagatgt taacaagcaa agcaacctct ctgcatttgc   360
agggaattgc aggggaagcc ttctctcagt ttatccctt cttagggcct ctttgcattt   420
gcagggaggg cttatctcgg tttattcttc ttcatactct acctgagtgg aacttttgat   480
gctgagttgt cttagcctat ttttttttgcc ca                                512
```

<210> SEQ ID NO 112
<211> LENGTH: 22
<212> TYPE: DNA
<213> ORGANISM: Artificial
<220> FEATURE:
<223> OTHER INFORMATION: PHM10028 FE primer

<400> SEQUENCE: 112

```
gcaaggaaac tgacattttt ag                                             22
```

<210> SEQ ID NO 113
<211> LENGTH: 22
<212> TYPE: DNA
<213> ORGANISM: Artificial
<220> FEATURE:
<223> OTHER INFORMATION: PHM10028 FI primer

<400> SEQUENCE: 113

```
tttgtgagac tcaattctca ta                                             22
```

<210> SEQ ID NO 114
<211> LENGTH: 21

```
<212> TYPE: DNA
<213> ORGANISM: Artificial
<220> FEATURE:
<223> OTHER INFORMATION: PHM10028 RI primer

<400> SEQUENCE: 114
caactatcgg atccgttagt t                                              21

<210> SEQ ID NO 115
<211> LENGTH: 22
<212> TYPE: DNA
<213> ORGANISM: Artificial
<220> FEATURE:
<223> OTHER INFORMATION: PHM10028 RE primer

<400> SEQUENCE: 115
cattgattgc acctgataaa tg                                             22

<210> SEQ ID NO 116
<211> LENGTH: 22
<212> TYPE: DNA
<213> ORGANISM: Artificial
<220> FEATURE:
<223> OTHER INFORMATION: PHM741 FE primer

<400> SEQUENCE: 116
agttctgtca aattcgttct gt                                             22

<210> SEQ ID NO 117
<211> LENGTH: 21
<212> TYPE: DNA
<213> ORGANISM: Artificial
<220> FEATURE:
<223> OTHER INFORMATION: PHM741 FI primer

<400> SEQUENCE: 117
tgtccatcaa agcaattcca g                                              21

<210> SEQ ID NO 118
<211> LENGTH: 22
<212> TYPE: DNA
<213> ORGANISM: Artificial
<220> FEATURE:
<223> OTHER INFORMATION: PHM741 RI primer

<400> SEQUENCE: 118
tttgtaacct gttcaaggca gt                                             22

<210> SEQ ID NO 119
<211> LENGTH: 22
<212> TYPE: DNA
<213> ORGANISM: Artificial
<220> FEATURE:
<223> OTHER INFORMATION: PHM741 RE primer

<400> SEQUENCE: 119
cgttctacgc aaaaaacatg at                                             22

<210> SEQ ID NO 120
<211> LENGTH: 19
<212> TYPE: DNA
<213> ORGANISM: Artificial
<220> FEATURE:
<223> OTHER INFORMATION: PHM6289 FE primer

<400> SEQUENCE: 120
```
ctctgatcga gcctattcc                                        19

<210> SEQ ID NO 121
<211> LENGTH: 21
<212> TYPE: DNA
<213> ORGANISM: Artificial
<220> FEATURE:
<223> OTHER INFORMATION: PHM6289 FI primer

<400> SEQUENCE: 121
acgaccatca ataatctgtc g                                     21

<210> SEQ ID NO 122
<211> LENGTH: 19
<212> TYPE: DNA
<213> ORGANISM: Artificial
<220> FEATURE:
<223> OTHER INFORMATION: PHM6289 RI primer

<400> SEQUENCE: 122
ttcgaccata cacgccagc                                        19

<210> SEQ ID NO 123
<211> LENGTH: 22
<212> TYPE: DNA
<213> ORGANISM: Artificial
<220> FEATURE:
<223> OTHER INFORMATION: PHM6289 RE primer

<400> SEQUENCE: 123
tcttttgttg gtgtgttcag tt                                    22

<210> SEQ ID NO 124
<211> LENGTH: 18
<212> TYPE: DNA
<213> ORGANISM: Artificial
<220> FEATURE:
<223> OTHER INFORMATION: PHM13089 FE primer

<400> SEQUENCE: 124
tccggcctcg cttgccat                                         18

<210> SEQ ID NO 125
<211> LENGTH: 18
<212> TYPE: DNA
<213> ORGANISM: Artificial
<220> FEATURE:
<223> OTHER INFORMATION: PHM13089 FI primer

<400> SEQUENCE: 125
gcccacgggc aacaagag                                         18

<210> SEQ ID NO 126
<211> LENGTH: 20
<212> TYPE: DNA
<213> ORGANISM: Artificial
<220> FEATURE:
<223> OTHER INFORMATION: PHM13089 RI primer

<400> SEQUENCE: 126
cttgccgtgt ctagggaact                                       20

<210> SEQ ID NO 127
<211> LENGTH: 20
<212> TYPE: DNA
<213> ORGANISM: Artificial

```
<220> FEATURE:
<223> OTHER INFORMATION: PHM13089 RE primer

<400> SEQUENCE: 127
acaaatactg gcactgattg                                              20

<210> SEQ ID NO 128
<211> LENGTH: 20
<212> TYPE: DNA
<213> ORGANISM: Artificial
<220> FEATURE:
<223> OTHER INFORMATION: PHM2305 FE primer

<400> SEQUENCE: 128
gatccatttg atcaggatga                                              20

<210> SEQ ID NO 129
<211> LENGTH: 22
<212> TYPE: DNA
<213> ORGANISM: Artificial
<220> FEATURE:
<223> OTHER INFORMATION: PHM2305 FI primer

<400> SEQUENCE: 129
ttatgccaaa ctcactgatg ag                                           22

<210> SEQ ID NO 130
<211> LENGTH: 21
<212> TYPE: DNA
<213> ORGANISM: Artificial
<220> FEATURE:
<223> OTHER INFORMATION: PHM2305 RI primer

<400> SEQUENCE: 130
attgtaacaa aaggcagcag c                                            21

<210> SEQ ID NO 131
<211> LENGTH: 20
<212> TYPE: DNA
<213> ORGANISM: Artificial
<220> FEATURE:
<223> OTHER INFORMATION: PHM2305 RE primer

<400> SEQUENCE: 131
tagctctcga gcaaacacga                                              20

<210> SEQ ID NO 132
<211> LENGTH: 20
<212> TYPE: DNA
<213> ORGANISM: Artificial
<220> FEATURE:
<223> OTHER INFORMATION: PHM9867 FE primer

<400> SEQUENCE: 132
tgacgacgac tcgatcttct                                              20

<210> SEQ ID NO 133
<211> LENGTH: 20
<212> TYPE: DNA
<213> ORGANISM: Artificial
<220> FEATURE:
<223> OTHER INFORMATION: PHM9867 FI primer

<400> SEQUENCE: 133
gatgagcctc cgtttgactt                                              20
```

-continued

```
<210> SEQ ID NO 134
<211> LENGTH: 22
<212> TYPE: DNA
<213> ORGANISM: Artificial
<220> FEATURE:
<223> OTHER INFORMATION: PHM9867 RI primer

<400> SEQUENCE: 134
tcaatgagtg aggtttctaa ct                                              22

<210> SEQ ID NO 135
<211> LENGTH: 22
<212> TYPE: DNA
<213> ORGANISM: Artificial
<220> FEATURE:
<223> OTHER INFORMATION: PHM9867 RE primer

<400> SEQUENCE: 135
attctactgg catgtaaaca tc                                              22

<210> SEQ ID NO 136
<211> LENGTH: 20
<212> TYPE: DNA
<213> ORGANISM: Artificial
<220> FEATURE:
<223> OTHER INFORMATION: PHM7775 FE primer

<400> SEQUENCE: 136
cgcatatccg ctttgaacga                                                 20

<210> SEQ ID NO 137
<211> LENGTH: 20
<212> TYPE: DNA
<213> ORGANISM: Artificial
<220> FEATURE:
<223> OTHER INFORMATION: PHM7775 FI primer

<400> SEQUENCE: 137
ccggcaaact tgttcaggaa                                                 20

<210> SEQ ID NO 138
<211> LENGTH: 22
<212> TYPE: DNA
<213> ORGANISM: Artificial
<220> FEATURE:
<223> OTHER INFORMATION: PHM7775 RI primer

<400> SEQUENCE: 138
agaatatgta gtagcggttg tt                                              22

<210> SEQ ID NO 139
<211> LENGTH: 21
<212> TYPE: DNA
<213> ORGANISM: Artificial
<220> FEATURE:
<223> OTHER INFORMATION: PHM7775 RE primer

<400> SEQUENCE: 139
aatgttccga catagccaat g                                               21

<210> SEQ ID NO 140
<211> LENGTH: 20
<212> TYPE: DNA
<213> ORGANISM: Artificial
<220> FEATURE:
<223> OTHER INFORMATION: PHM16407 FE primer
```

```
<400> SEQUENCE: 140
gtgatctgga gagagattcc                                              20

<210> SEQ ID NO 141
<211> LENGTH: 21
<212> TYPE: DNA
<213> ORGANISM: Artificial
<220> FEATURE:
<223> OTHER INFORMATION: PHM16407 FI primer

<400> SEQUENCE: 141
tagctctgga gaagttcaac a                                            21

<210> SEQ ID NO 142
<211> LENGTH: 22
<212> TYPE: DNA
<213> ORGANISM: Artificial
<220> FEATURE:
<223> OTHER INFORMATION: PHM16407 RI primer

<400> SEQUENCE: 142
gcatgtaact ctagtttatg gt                                           22

<210> SEQ ID NO 143
<211> LENGTH: 22
<212> TYPE: DNA
<213> ORGANISM: Artificial
<220> FEATURE:
<223> OTHER INFORMATION: PHM16407 RE primer

<400> SEQUENCE: 143
ggcatattca tcatactatt cg                                           22

<210> SEQ ID NO 144
<211> LENGTH: 20
<212> TYPE: DNA
<213> ORGANISM: Artificial
<220> FEATURE:
<223> OTHER INFORMATION: PHM14523 FE primer

<400> SEQUENCE: 144
tgcactacct tcacactgga                                              20

<210> SEQ ID NO 145
<211> LENGTH: 21
<212> TYPE: DNA
<213> ORGANISM: Artificial
<220> FEATURE:
<223> OTHER INFORMATION: PHM14523 FI primer

<400> SEQUENCE: 145
tgactgagaa gtcggatgtc t                                            21

<210> SEQ ID NO 146
<211> LENGTH: 19
<212> TYPE: DNA
<213> ORGANISM: Artificial
<220> FEATURE:
<223> OTHER INFORMATION: PHM14523 RI primer

<400> SEQUENCE: 146
gtcacgcaca tttacctcc                                               19

<210> SEQ ID NO 147
```

```
<211> LENGTH: 21
<212> TYPE: DNA
<213> ORGANISM: Artificial
<220> FEATURE:
<223> OTHER INFORMATION: PHM14523 RE primer

<400> SEQUENCE: 147
catgatctct ctcacgtaaa c                                              21

<210> SEQ ID NO 148
<211> LENGTH: 20
<212> TYPE: DNA
<213> ORGANISM: Artificial
<220> FEATURE:
<223> OTHER INFORMATION: PHM2916 FE primer

<400> SEQUENCE: 148
caccgttgag aactttctgc                                                20

<210> SEQ ID NO 149
<211> LENGTH: 22
<212> TYPE: DNA
<213> ORGANISM: Artificial
<220> FEATURE:
<223> OTHER INFORMATION: PHM2916 FI primer

<400> SEQUENCE: 149
caacttgtca acattccctc at                                             22

<210> SEQ ID NO 150
<211> LENGTH: 22
<212> TYPE: DNA
<213> ORGANISM: Artificial
<220> FEATURE:
<223> OTHER INFORMATION: PHM2916 RI primer

<400> SEQUENCE: 150
taagaataca acatgtcgag tg                                             22

<210> SEQ ID NO 151
<211> LENGTH: 21
<212> TYPE: DNA
<213> ORGANISM: Artificial
<220> FEATURE:
<223> OTHER INFORMATION: PHM2916 RE primer

<400> SEQUENCE: 151
tttgcaacga atactccacc t                                              21

<210> SEQ ID NO 152
<211> LENGTH: 21
<212> TYPE: DNA
<213> ORGANISM: Artificial
<220> FEATURE:
<223> OTHER INFORMATION: PHM4583 FE primer

<400> SEQUENCE: 152
cccaagaact ctttgaaact c                                              21

<210> SEQ ID NO 153
<211> LENGTH: 18
<212> TYPE: DNA
<213> ORGANISM: Artificial
<220> FEATURE:
<223> OTHER INFORMATION: PHM4583 FI primer

<400> SEQUENCE: 153
```

```
tttctttcag gtagatga                                                    18
```

<210> SEQ ID NO 154
<211> LENGTH: 19
<212> TYPE: DNA
<213> ORGANISM: Artificial
<220> FEATURE:
<223> OTHER INFORMATION: PHM4583 RI primer

<400> SEQUENCE: 154

```
acttaaaata aataggcat                                                   19
```

<210> SEQ ID NO 155
<211> LENGTH: 22
<212> TYPE: DNA
<213> ORGANISM: Artificial
<220> FEATURE:
<223> OTHER INFORMATION: PHM4583 RE primer

<400> SEQUENCE: 155

```
tttggccttc atatttcatt cg                                               22
```

<210> SEQ ID NO 156
<211> LENGTH: 661
<212> TYPE: DNA
<213> ORGANISM: artificial
<220> FEATURE:
<223> OTHER INFORMATION: PHM14165 reference sequence

<400> SEQUENCE: 156

```
gaactgcaga acagctgacg gtggtgacta gatagactac cggcatcatc agtaacataa      60
taagtaactg cgtaacaggg atactacatg tatgtctgtg cagtaacagt gacattattt     120
tctgcaggtg gaacttgaaa gatgcaacga gactttctgc ttacccacag ctccacggat     180
tgtctacggg ctgaaggggt cgtcggctga catgttcctc gacaacgcgg aatacaggaa     240
gttccttttc cgagagtttg gggtgtctac aatggacgag gagagcgcag cggtggtgat     300
ggtcagctca gctcccttac tcatacagtc atacttgcac tacgtacatc ccgaccatgt     360
atgttactta ctagtaagat aaatttagcg ctcaactctg atgatcagac agcaacgtcg     420
cctggcatac ccgtgatcgt gttccgagga gtgtctgact tggctggagg ggagccgaca     480
tggtcgtcca caagcctgat gaacctggcg tccattaatg cattaaaagt ggcggtagag     540
ttcatcgctg cagttggcaa gcatagttca accgcatcag taaaaagatg atcgccatcc     600
tcgtcctttg ctgctccaaa ataggcctgc gcagtaactg attatagttt ttaataaaat     660
a                                                                     661
```

<210> SEQ ID NO 157
<211> LENGTH: 507
<212> TYPE: DNA
<213> ORGANISM: artificial
<220> FEATURE:
<223> OTHER INFORMATION: PHM15960 reference sequence

<400> SEQUENCE: 157

```
tttymagtac cccacccttg gcggcctcat caagtggcag gtgccctgga cgcgaagcag      60
cggaagctgc agctggtgaa caagctgtgg acggacccca cgaccaggt gcacatcgac      120
gagagcgcgg ggctggtggc ccggctggtg ggcttctgcg agggcggcaa catcagcaag     180
gagatgttcg agctcaactt cgccgtcccc acgagcagga ggccgtggct ggtgggctgg     240
```

```
caaccaatct cgaacatgat cagggagaag acccagcagc tctggtgaga actgaacgca    300
tcatggcgca gcgccgtgtt gtacagatgg aatggaacaa gagacagaca gtgcatttcg    360
gtttcagctc tggaaattgc tgatcaatta attgtggggg gaagcgtctc tacttccttc    420
ccggttgatc aaggcggaca gcggtcgtc ggtctggtat cccttcctg tgtccctaaa      480 tgtagatggt catagctgtt ccacccc                                        507

<210> SEQ ID NO 158
<211> LENGTH: 740
<212> TYPE: DNA
<213> ORGANISM: artificial
<220> FEATURE:
<223> OTHER INFORMATION: PHM8438 reference sequence

<400> SEQUENCE: 158
aaacggaacr aaacttcccc ggaacgggga acatggccaa gttcccagtt cccgggtaat     60
aagccgaatt ccgaagaagt ccctttgttc catggcaatg ggtcttttat ttaagtttct    120
tgttacagta tgcccaagta caaaaaaaat ctttcttttg cttggcttgg cttgcaagtt    180
tgacaagcta tttgatggac aaatcagcag gctgcgcatg tctgatctac attttgagcc    240
tgtcatttag gattacttgg gtaatatttta gtttatcaaa ctggtgtttg caggtagtac    300
ttggcgagga atcgcacaac gtacatgaca tgtcatttgt catatgcatc gcaaggtcca    360
ccccaattat ttcaccagat cttctttctc atgcctcagg taaatctcgc tgaatccaga    420
gtacaattgt gaactaccca tgcagacagt agctatttca attttgacac tgcagtcctg    480
tggacagtct gaataatttt atgcacgtac tctgatgaaa caggcaacag caatcatgtc    540
gaggcgttga gagtatatct tctgtcaaaa tctctatcca gattgaagaa ccagttccaa    600
agtggaaatg gcgtggtaag aagtcaacgc cgtatgcttc gtccttcctt ttcagaaagg    660
gtattccttt tttgcttata acttgtctac actcttccag attacgtcga ctgcatcggg    720
gtaaagaacg ttattaagta                                                740

<210> SEQ ID NO 159
<211> LENGTH: 548
<212> TYPE: DNA
<213> ORGANISM: artificial
<220> FEATURE:
<223> OTHER INFORMATION: PHM9867 reference sequence

<400> SEQUENCE: 159
aaaaaaaccc aatccaacag atgagcctcc gtttgacttc ggcgatggcg acacggagct     60
tgaaggcatt ttccggagcg gtgtcgggtg ggagctgctc ccggtgccgc tggacgagga    120
cgagttcgag gtgctgccgg ggcacgtcgt ggaagtgggc ggcgccccgc cggcggcgcg    180
cgcagtggtg gagcggctcc aggtggtggc cgtcagaggc gaggaggttg tgcaggagtg    240
cgctgtttgc aaggaaggga tggaacaggg ggagctcacc actgggctgc cgtgtgggca    300
tttctaccac ggggcgtgca ttggtccatg gcttgccatc cggaacacgt gcccggtgtg    360
ccggtatgag ctgcctactg atgaccctga gtatgagaag cggaggacga ggcgccattc    420
tgctggtggt tcaacaccac agttgggtgc accgatgcag gtttgagcta gggctgattg    480
gtgctatgtc ttggatgcaa ttccatcatt ccacggaagt taaaacctca ctcatacttt    540
ccttaata                                                             548

<210> SEQ ID NO 160
<211> LENGTH: 535
```

```
<212> TYPE: DNA
<213> ORGANISM: artificial
<220> FEATURE:
<223> OTHER INFORMATION: PHM14523 reference sequence

<400> SEQUENCE: 160
atatcccagt cacaacgtga ctgagaagca aatgtctact ctttcggtgt tgttttgctt      60
gaggttcttt gtgcaaggcc agtgatcgac cccacgctgc cgagggagat ggtgaacctg     120
gccgagtggg ggatgaagtg cagaagaga ggagagctgc accagatcat cgatcagagg      180
atctcgggca caatcaggcc ggactctctg aggaagtttg gcgagaccgt ggagaagtgc     240
ctggcagact acggcgtgga gcggccgtcg atgggagacg tcctctggaa cctggagtac     300
gttctgcagc ttcaggacgc cgattcgacg gtctcggatg tgaacagcat gaaccgtatc     360
gtggaactcc cgtcacaggt ccagaacgtc ggggccctcg agagcatcag cgtgacgatg     420
gcagaagccg agcgtcaaa cgagcctgac cacgacctct ccgatgtgtc catgagccgc      480
gtcttctctc agctgatcaa ggccgaggga gtaaattgct aaattttaa aaaaa           535

<210> SEQ ID NO 161
<211> LENGTH: 20
<212> TYPE: DNA
<213> ORGANISM: artificial
<220> FEATURE:
<223> OTHER INFORMATION: Primer

<400> SEQUENCE: 161
agtacagaaa cgaggagctt                                                  20

<210> SEQ ID NO 162
<211> LENGTH: 20
<212> TYPE: DNA
<213> ORGANISM: artificial
<220> FEATURE:
<223> OTHER INFORMATION: Primer

<400> SEQUENCE: 162
gttcagaact gcagaacagc                                                  20

<210> SEQ ID NO 163
<211> LENGTH: 21
<212> TYPE: DNA
<213> ORGANISM: artificial
<220> FEATURE:
<223> OTHER INFORMATION: Primer

<400> SEQUENCE: 163
aagtaacttc cagttactgc c                                                21

<210> SEQ ID NO 164
<211> LENGTH: 21
<212> TYPE: DNA
<213> ORGANISM: artificial
<220> FEATURE:
<223> OTHER INFORMATION: Primer

<400> SEQUENCE: 164
ttatgacttg aagccacaag g                                                21

<210> SEQ ID NO 165
<211> LENGTH: 20
<212> TYPE: DNA
<213> ORGANISM: artificial
<220> FEATURE:
```

<223> OTHER INFORMATION: Primer

<400> SEQUENCE: 165
agaaggatgg gatcaaggct                                               20

<210> SEQ ID NO 166
<211> LENGTH: 20
<212> TYPE: DNA
<213> ORGANISM: artificial
<220> FEATURE:
<223> OTHER INFORMATION: Primer

<400> SEQUENCE: 166
tgagcggctc ttcatcaagt                                               20

<210> SEQ ID NO 167
<211> LENGTH: 20
<212> TYPE: DNA
<213> ORGANISM: artificial
<220> FEATURE:
<223> OTHER INFORMATION: Primer

<400> SEQUENCE: 167
ctacatttag ggacacagga                                               20

<210> SEQ ID NO 168
<211> LENGTH: 20
<212> TYPE: DNA
<213> ORGANISM: artificial
<220> FEATURE:
<223> OTHER INFORMATION: Primer

<400> SEQUENCE: 168
tcagattctt cggactccac                                               20

<210> SEQ ID NO 169
<211> LENGTH: 22
<212> TYPE: DNA
<213> ORGANISM: artificial
<220> FEATURE:
<223> OTHER INFORMATION: Primer

<400> SEQUENCE: 169
agaaattacg aaagactgct ca                                            22

<210> SEQ ID NO 170
<211> LENGTH: 21
<212> TYPE: DNA
<213> ORGANISM: artificial
<220> FEATURE:
<223> OTHER INFORMATION: Primer

<400> SEQUENCE: 170
ttggctcacc aatcgttcca a                                             21

<210> SEQ ID NO 171
<211> LENGTH: 20
<212> TYPE: DNA
<213> ORGANISM: artificial
<220> FEATURE:
<223> OTHER INFORMATION: Primer

<400> SEQUENCE: 171
gataaccttc gatgcagtcg                                               20

```
<210> SEQ ID NO 172
<211> LENGTH: 21
<212> TYPE: DNA
<213> ORGANISM: artificial
<220> FEATURE:
<223> OTHER INFORMATION: Primer

<400> SEQUENCE: 172
taggatcgac tagccagata a                                          21

<210> SEQ ID NO 173
<211> LENGTH: 20
<212> TYPE: DNA
<213> ORGANISM: artificial
<220> FEATURE:
<223> OTHER INFORMATION: Primer

<400> SEQUENCE: 173
tgacgacgac tcgatcttct                                            20

<210> SEQ ID NO 174
<211> LENGTH: 20
<212> TYPE: DNA
<213> ORGANISM: artificial
<220> FEATURE:
<223> OTHER INFORMATION: Primer

<400> SEQUENCE: 174
gatgagcctc cgtttgactt                                            20

<210> SEQ ID NO 175
<211> LENGTH: 22
<212> TYPE: DNA
<213> ORGANISM: artificial
<220> FEATURE:
<223> OTHER INFORMATION: Primer

<400> SEQUENCE: 175
tcaatgagtg aggtttctaa ct                                         22

<210> SEQ ID NO 176
<211> LENGTH: 22
<212> TYPE: DNA
<213> ORGANISM: artificial
<220> FEATURE:
<223> OTHER INFORMATION: Primer

<400> SEQUENCE: 176
attctactgg catgtaaaca tc                                         22

<210> SEQ ID NO 177
<211> LENGTH: 20
<212> TYPE: DNA
<213> ORGANISM: artificial
<220> FEATURE:
<223> OTHER INFORMATION: Primer

<400> SEQUENCE: 177
tgcactacct tcacactgga                                            20

<210> SEQ ID NO 178
<211> LENGTH: 21
<212> TYPE: DNA
<213> ORGANISM: artificial
<220> FEATURE:
<223> OTHER INFORMATION: Primer
```

```
<400> SEQUENCE: 178
tgactgagaa gtcggatgtc t                                              21

<210> SEQ ID NO 179
<211> LENGTH: 19
<212> TYPE: DNA
<213> ORGANISM: artificial
<220> FEATURE:
<223> OTHER INFORMATION: Primer

<400> SEQUENCE: 179
gtcacgcaca tttacctcc                                                 19

<210> SEQ ID NO 180
<211> LENGTH: 21
<212> TYPE: DNA
<213> ORGANISM: artificial
<220> FEATURE:
<223> OTHER INFORMATION: Primer

<400> SEQUENCE: 180
catgatctct ctcacgtaaa c                                              21
```

COMPOSITIONS AND METHODS TO SELECT FOR REDUCED GRAIN MOISTURE IN MAIZE

CROSS REFERENCE TO RELATED APPLICATIONS

Figure 1:
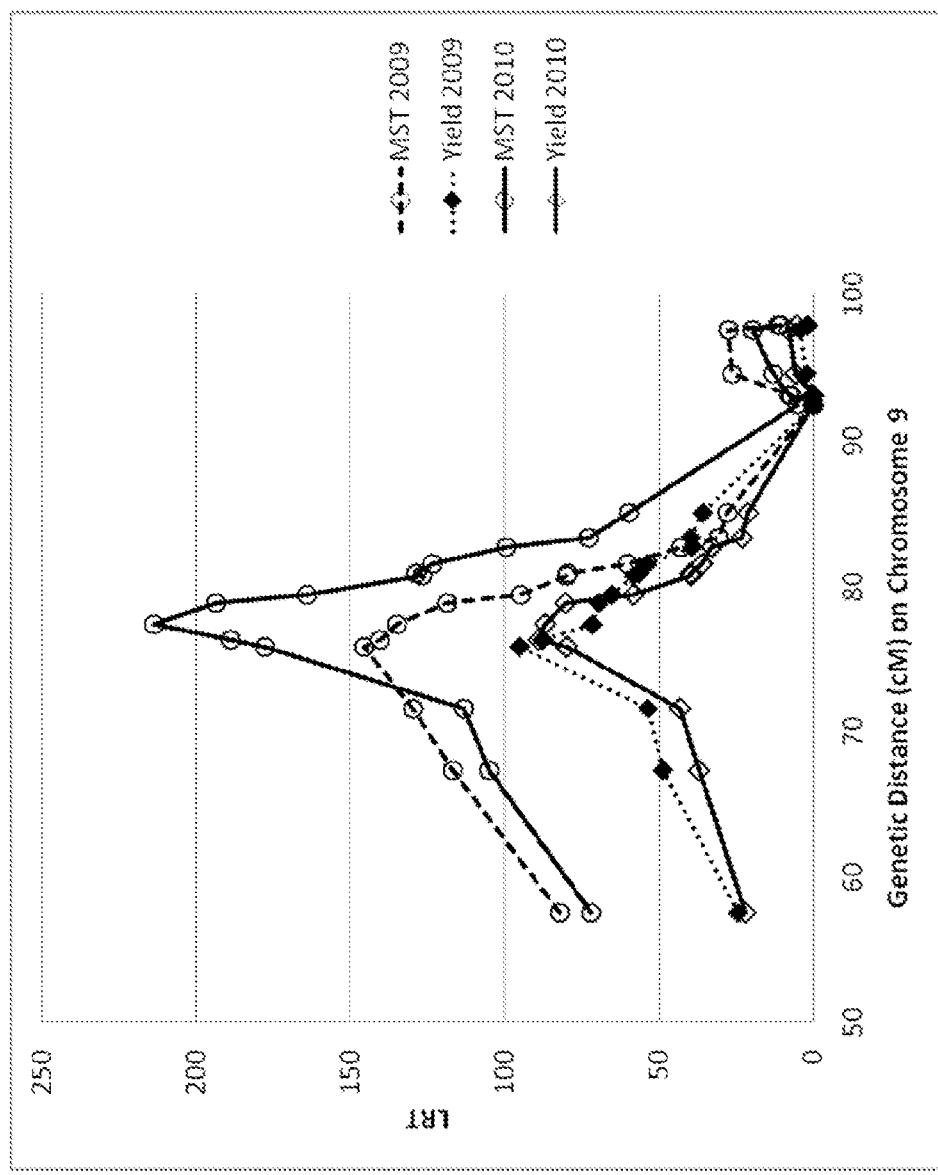

This application claims the benefit of U.S. Provisional Application No. 61/602,188, filed Feb. 23, 2012, the entire content of which is herein incorporated by reference.

FIELD OF THE INVENTION

The present disclosure relates to compositions and methods useful in selecting maize plants with reduced grain moisture.

BACKGROUND OF THE INVENTION

Grain moisture is of primary importance for maize (*Zea mays* L.) production and breeding. Low (or reduced) grain moisture decreases the economic impact of artificial drying and allows earlier harvesting, which permits the grower to obtain a higher price for the crop at an earlier date and reduces exposure of the crop to adverse weather and field conditions that hinder the harvest operation (Sweeney et al (1994) *Crop Sci* 34:391-396). Warmer temperatures and lower humidity promote rapid field drying of corn grain. However, in mid- to short-season environments, harvest time is often characterized by decreases in temperature and increases in humidity. Thus, hybrids with superior yielding ability that dry at a more rapid rate are highly desirable.

Historically, selection of inbred lines to produce hybrids with reduced grain moisture has been performed by measuring grain moisture directly. However, some studies have suggested that grain moisture can also be selected for indirectly by measuring traits such as field grain drying rate (FDR) (Sala et al (2006) *Theor Appl Genet* 112:462-471) or husk senescence (Sweeney et al (1994) *Crop Sci* 34:391-396). Silking date and black layer formation were also found to be significantly correlated with grain moisture in some studies; however, other studies have shown a limited association (Sweeney et al (1994) *Crop Sci* 34:391-396). The use of any phenotypic selection method can require extensive resources and is somewhat imprecise, with environmental factors and complex associations between different agronomic traits complicating selection.

Selection through the use of molecular markers associated with reduced grain moisture allows selections based solely on the genetic composition of the progeny. As a result, plant breeding can occur more rapidly, thereby generating commercially acceptable maize plants with reduced grain moisture in a relatively short amount of time. Thus, it is desirable to provide compositions and methods for identifying and selecting maize plants with reduced grain moisture. These plants can be used in breeding programs to generate high-yielding hybrids that dry at a more rapid rate.

QTL for grain moisture have been reported on chromosome 9 (Frascaroli et al. (2007) *Genetics* 176:625-644; Sala et al. (2005) *Theor Appl Genet* 112:462-471; Blanc et al. (2006) *Theor Appl Genet* 113:206-224; Moreau et al. (2004) *Theor Appl Genet* 110:92-105; Lu et al. (2003) *Theor Appl Genet* 107:494-502; Austin et al. (2000) *Crop Sci.* 40:30-39).

SUMMARY OF THE INVENTION

Compositions and methods for selecting maize plants for grain moisture are provided herein, including compositions and methods for identifying and selecting maize plants with reduced grain moisture.

In one embodiment, methods for identifying and/or selecting a maize plant with reduced grain moisture are presented in which a marker allele is detected in the maize plant. The marker is located on chromosome 9 at 72-79 cM on a single meiosis map or at 200.4-230.6 cM on an IBM2 map; and an allele of the marker is associated with reduced grain moisture. Maize plants that have one or more marker alleles associated with reduced grain moisture are then identified and/or selected. The maize plant may be an inbred in the Stiff Stalk Synthetic heterotic group or may be a progeny plant derived from an inbred in the Stiff Stalk Synthetic heterotic group.

In one aspect, the marker is PHM18206, PHM9929, PHM6726, PHM4910, PHM6667, PHM229, PHM6567, PHM5208, PHM15758, PHM14370, PHM3159, PHM17246, or PHM4691.

In another aspect, the marker detects a SNP polymorphism. The SNP polymorphism can be PHM18206-5, PHM9929-8, PHM6726-10, PHM4910-5, PHM6667-11, PHM229-15, PHM6567-10, PHM5208-11, PHM15758-6, PHM14370-9, PHM3159-14, PHM17246-16, or PHM4691-9.

In another aspect, the allele is a "T" at PHM18206-5, a "T" at PHM9929-8, an "A" at PHM6726-10, a "G" at PHM4910-5, a "T" at PHM6667-11, a "C" at PHM229-15, a "T" at PHM6567-10, a "T" at PHM5208-11, a "C" at PHM15758-6, a "G" at PHM14370-9, a "C" at PHM3159-14, a "T" at PHM17246-16, or a "T" at PHM4691-9.

In another embodiment, methods for identifying and/or selecting a maize plant with reduced grain moisture are presented in which a marker allele is detected in the maize plant. The marker is located in a chromosomal interval defined by and including PHM18206 and PHM4910; and an allele of the marker is associated with reduced grain moisture. Maize plants that have one or more marker alleles associated with reduced grain moisture are then identified and/or selected. The maize plant may be an inbred in the Stiff Stalk Synthetic heterotic group or may be a progeny plant derived from an inbred in the Stiff Stalk Synthetic heterotic group.

In one aspect, the marker is PHM18206, PHM9929, PHM6726, PHM4910, PHM6667, PHM229, PHM6567, PHM5208, PHM15758, PHM14370, PHM3159, PHM17246, or PHM4691.

In another aspect, the marker detects a SNP polymorphism. The SNP polymorphism can be PHM18206-5, PHM9929-8, PHM6726-10, PHM4910-5, PHM6667-11, PHM229-15, PHM6567-10, PHM5208-11, PHM15758-6, PHM14370-9, PHM3159-14, PHM17246-16, or PHM4691-9.

In another aspect, the allele is a "T" at PHM18206-5, a "T" at PHM9929-8, an "A" at PHM6726-10, a "G" at PHM4910-5, a "T" at PHM6667-11, a "C" at PHM229-15, a "T" at PHM6567-10, a "T" at PHM5208-11, a "C" at PHM15758-6, a "G" at PHM14370-9, a "C" at PHM3159-14, a "T" at PHM17246-16, or a "T" at PHM4691-9.

In another embodiment, methods for identifying and/or selecting a maize plant with reduced grain moisture are presented in which a marker allele is detected in the maize plant. The marker is located on chromosome 9 at 93-98 cM on a single meiosis map or at 317-323 cM on an IBM2 map;

and an allele of the marker is associated with reduced grain moisture. Maize plants that have one or more marker alleles associated with reduced grain moisture are then identified and/or selected. The maize plant may be an inbred in the Stiff Stalk Synthetic heterotic group, or may be a progeny plant derived from an inbred in the Stiff Stalk Synthetic heterotic group.

In one aspect, the marker is PHM10270, PHM4598, PHM14092, PHM18292, PHM3507, PHM3004, or PHM14122.

In another aspect, the marker detects a SNP polymorphism. The SNP polymorphism can be PHM10270-13, PHM4598-22, PHM14092-77, PHM18292-9, PHM3507-13, PHM3004-13, or PHM14122-22.

In another aspect, the allele is a "C" at PHM10270-13, a "C" at PHM4598-22, a "C" at PHM14092-77, an "A" at PHM18292-9, a "G" or an "A" at PHM3507-13, a "G" at PHM3004-13, or a "G" at PHM14122-22.

In another embodiment, methods for identifying and/or selecting a maize plant with reduced grain moisture are presented in which a marker allele is detected in the maize plant. The marker is located on in a chromosomal interval defined by and including PHM4598 and PHM14092; and an allele of the marker is associated with reduced grain moisture. Maize plants that have one or more marker alleles associated with reduced grain moisture are then identified and/or selected. The maize plant may be an inbred in the Stiff Stalk Synthetic heterotic group, or may be a progeny plant derived from an inbred in the Stiff Stalk Synthetic heterotic group.

In one embodiment, the marker is PHM10270, PHM4598, PHM14092, PHM18292, PHM3507, PHM3004, or PHM14122.

In another aspect, the marker detects a SNP polymorphism. The SNP polymorphism can be PHM10270-13, PHM4598-22, PHM14092-77, PHM18292-9, PHM3507-13, PHM3004-13, or PHM14122-22.

In another aspect, the allele is a "C" at PHM10270-13, a "C" at PHM4598-22, a "C" at PHM14092-77, an "A" at PHM18292-9, a "G" or an "A" at PHM3507-13, a "G" at PHM3004-13, or a "G" at PHM14122-22.

In another embodiment, methods for identifying and/or selecting a maize plant with reduced grain moisture are presented in which a haplotype is detected in the maize plant. The haplotype can comprise: a "T" at PHM9929-8, a "T" at PHM6667-11, a "C" at PHM229-15, a "T" at PHM6567-10, a "T" at PHM5208-11, a "C" at PHM15758-6, a "G" at PHM14370-9, a "C" at PHM3159-14, and a "T" at PHM17246-16. Maize plants that have the haplotype are identified and/or selected.

In another embodiment, methods for identifying and/or selecting a maize plant with reduced grain moisture are presented in which a haplotype is detected in the maize plant. The haplotype can comprise: a "C" at PHM10270-13, a "C" at PHM4598-22, a "C" at PHM14092-77, an "A" at PHM18292-9, a "G" or an "A" at PHM3507-13, a "G" at PHM3004-13, and a "G" at PHM14122-22. Maize plants that have the haplotype are identified and/or selected. The maize plant may be an inbred in the Stiff Stalk Synthetic heterotic group, or may be a progeny plant derived from an inbred in the Stiff Stalk Synthetic heterotic group.

In another embodiment, maize plants identified and/or selected by any of the methods presented above are included.

In another embodiment, a maize plant comprising within its genome a haplotype consisting of: a "T" at PHM9929-8, a "T" at PHM6667-11, a "C" at PHM229-15, a "T" at PHM6567-10, a "T" at PHM5208-11, a "C" at PHM15758-6, a "G" at PHM14370-9, a "C" at PHM3159-14, and a "T" at PHM17246-16; that exhibits reduced grain moisture when compared to a maize plant or progeny plant that does not have the haplotype, is presented. The maize plant may be an inbred in the Stiff Stalk Synthetic heterotic group, or may be a progeny plant derived from an inbred in the Stiff Stalk Synthetic heterotic group.

In another embodiment, a maize plant comprising within its genome a haplotype consisting of: a "C" at PHM10270-13, a "C" at PHM4598-22, a "C" at PHM14092-77, an "A" at PHM18292-9, a "G" or an "A" at PHM3507-13, a "G" at PHM3004-13, and a "G" at PHM14122-22; that exhibits reduced grain moisture when compared to a maize plant or progeny plant that does not have the haplotype, is presented. The maize plant may be an inbred in the Stiff Stalk Synthetic heterotic group, or may be a progeny plant derived from an inbred in the Stiff Stalk Synthetic heterotic group.

In another embodiment, methods of introgressing a reduced grain moisture QTL allele into a maize plant are provided. The methods include: screening a population with at least one marker to determine if one or more maize plants from the population comprise(s) an allele of a marker associated with a reduced grain moisture QTL allele, wherein the reduced grain moisture QTL allele comprises a "T" at PHM18206-5, a "T" at PHM9929-8, an "A" at PHM6726-10, a "G" at PHM4910-5, a "T" at PHM6667-11, a "C" at PHM229-15, a "T" at PHM6567-10, a "T" at PHM5208-11, a "C" at PHM15758-6, a "G" at PHM14370-9, a "C" at PHM3159-14, a "T" at PHM17246-16, and a "T" at PHM4691-9; and selecting from said population at least one maize plant comprising an allele of said marker locus associated with a reduced grain moisture QTL allele. A marker of interest can be located within 5 cM, 2 cM, or 1 cM of the grain moisture QTL.

In another embodiment, methods of introgressing a reduced grain moisture QTL allele into a maize plant are provided. The methods include: screening a population with at least one marker to determine if one or more maize plants from the population comprise(s) an allele of said marker associated with a reduced grain moisture QTL allele, wherein the reduced grain moisture QTL comprises: a "C" at PHM10270-13, a "C" at PHM4598-22, a "C" at PHM14092-77, an "A" at PHM18292-9, a "G" or an "A" at PHM3507-13, a "G" at PHM3004-13, and a "G" at PHM14122-22; and selecting from said population at least one maize plant comprising an allele of said marker locus associated with a reduced grain moisture QTL allele. A marker of interest can be located within 5 cM, 2 cM, or 1 cM of the grain moisture QTL.

BRIEF DESCRIPTION OF THE DRAWINGS AND SEQUENCE LISTINGS

The invention can be more fully understood from the following detailed description and the accompanying drawings and Sequence Listing which form a part of this application.

The sequence descriptions and Sequence Listing attached hereto comply with the rules governing nucleotide and/or amino acid sequence disclosures in patent applications as set forth in 37 C.F.R. §1.821 1.825. The Sequence Listing contains the one letter code for nucleotide sequence characters and the three letter codes for amino acids as defined in conformity with the IUPAC IUBMB standards described in Nucleic Acids Res. 13:3021 3030 (1985) and in the Biochemical J. 219 (2):345 373 (1984) which are herein incorporated by reference. The symbols and format used for nucleotide and amino acid sequence data comply with the rules set forth in 37 C.F.R. §1.822.

FIG. 1 depicts the results of a likelihood ratio test (LRT), which shows QTL locations for grain moisture (MS) and yield between 57.5 and 97.8 cM on chromosome 9 across 2 years of field testing. Dotted lines with unfilled circles represent the likelihood test ratios (LRTs) for grain moisture data collected in 2009 field trials. Dotted lines with filled diamonds represent the LRTs for yield data collected in 2009 field trials. Solid lines with unfilled circles represent the LRTs for grain moisture data collected in 2010 field trials. Solid lines with unfilled diamonds represent the LRTs for yield data collected in 2010 field trials.

Figure 2:
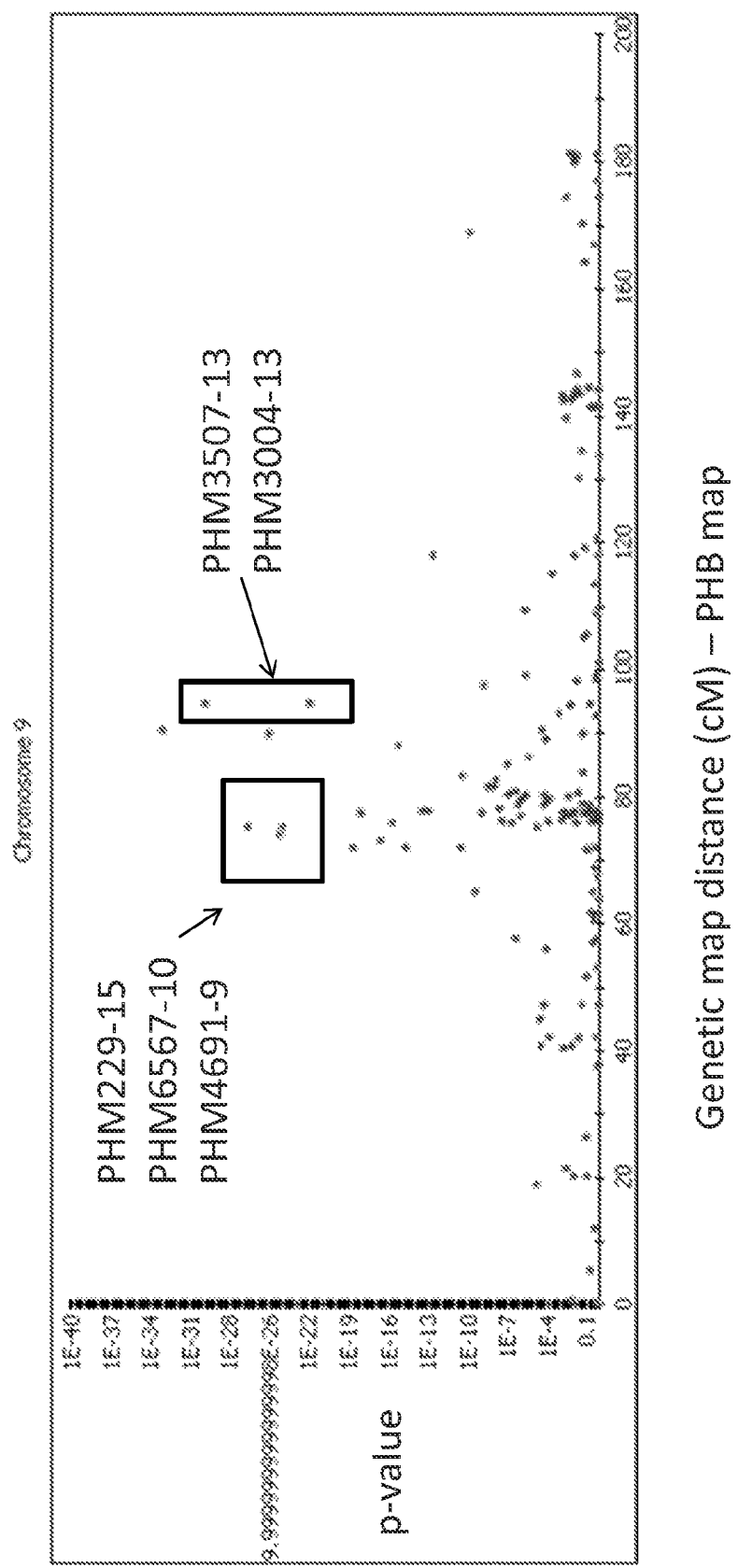

FIG. 2 shows the results of the association mapping analysis described in Example 3 used to detect markers associated with grain moisture. The association mapping analysis revealed two peaks that overlapped with QTL9-1 and QTL9-2. The x-axis represents the genetic map distance based on the PHB map, an internally derived single meiosis map. The y-axis represents the p-values for the marker-trait associations.

SEQ ID NO:1 is the reference sequence for marker PHM18206.
SEQ ID NO:2 is the reference sequence for marker PHM6567.
SEQ ID NO:3 is the reference sequence for marker PHM4691.
SEQ ID NO:4 is the reference sequence for marker PHM229.
SEQ ID NO:5 is the reference sequence for marker PHM9929.
SEQ ID NO:6 is the reference sequence for marker PHM3159.
SEQ ID NO:7 is the reference sequence for marker PHM15758.
SEQ ID NO:8 is the reference sequence for marker PHM5208.
SEQ ID NO:9 is the reference sequence for marker PHM6667.
SEQ ID NO:10 is the reference sequence for marker PHM17246.
SEQ ID NO:11 is the reference sequence for marker PHM14370.
SEQ ID NO:12 is the reference sequence for marker PHM6726.
SEQ ID NO:13 is the reference sequence for marker PHM4910.
SEQ ID NO:14 is the reference sequence for marker PHM4598.
SEQ ID NO:15 is the reference sequence for marker PHM3507.
SEQ ID NO:16 is the reference sequence for marker PHM18292.
SEQ ID NO:17 is the reference sequence for marker PHM3004.
SEQ ID NO:18 is the reference sequence for marker PHM14122.
SEQ ID NO:19 is the reference sequence for marker PHM10270
SEQ ID NO:20 is the reference sequence for marker PHM14092.
SEQ ID NO:21 is the PHM18206 forward external primer.
SEQ ID NO:22 is the PHM18206 forward internal primer.
SEQ ID NO:23 is the PHM18206 reverse internal primer.
SEQ ID NO:24 is the PHM18206 reverse external primer.
SEQ ID NO:25 is the PHM6567 forward external primer.
SEQ ID NO:26 is the PHM6567 forward internal primer.
SEQ ID NO:27 is the PHM6567 reverse internal primer.
SEQ ID NO:28 is the PHM6567 reverse external primer.
SEQ ID NO:29 is the PHM4691 forward external primer.
SEQ ID NO:30 is the PHM4691 forward internal primer.
SEQ ID NO:31 is the PHM4691 reverse internal primer.
SEQ ID NO:32 is the PHM4691 reverse external primer.
SEQ ID NO:33 is the PHM229 forward external primer.
SEQ ID NO:34 is the PHM229 forward internal primer.
SEQ ID NO:35 is the PHM229 reverse internal primer.
SEQ ID NO:36 is the PHM229 reverse external primer.
SEQ ID NO:37 is the PHM9929 forward external primer.
SEQ ID NO:38 is the PHM9929 forward internal primer.
SEQ ID NO:39 is the PHM9929 reverse internal primer.
SEQ ID NO:40 is the PHM9929 reverse external primer.
SEQ ID NO:41 is the PHM3159 forward external primer.
SEQ ID NO:42 is the PHM3159 forward internal primer.
SEQ ID NO:43 is the PHM3159 reverse internal primer.
SEQ ID NO:44 is the PHM3159 reverse external primer.
SEQ ID NO:45 is the PHM15758 forward external primer.
SEQ ID NO:46 is the PHM15758 forward internal primer.
SEQ ID NO:47 is the PHM15758 reverse internal primer.
SEQ ID NO:48 is the PHM15758 reverse external primer.
SEQ ID NO:49 is the PHM5208 forward external primer.
SEQ ID NO:50 is the PHM5208 forward internal primer.
SEQ ID NO:51 is the PHM5208 reverse internal primer.
SEQ ID NO:52 is the PHM5208 reverse external primer.
SEQ ID NO:53 is the PHM6667 forward external primer.
SEQ ID NO:54 is the PHM6667 forward internal primer.
SEQ ID NO:55 is the PHM6667 reverse internal primer.
SEQ ID NO:56 is the PHM6667 reverse external primer.
SEQ ID NO:57 is the PHM17246 forward external primer.
SEQ ID NO:58 is the PHM17246 forward internal primer.
SEQ ID NO:59 is the PHM17246 reverse internal primer.
SEQ ID NO:60 is the PHM17246 reverse external primer.
SEQ ID NO:61 is the PHM14370 forward external primer.
SEQ ID NO:62 is the PHM14370 forward internal primer.
SEQ ID NO:63 is the PHM14370 reverse internal primer.
SEQ ID NO:64 is the PHM14370 reverse external primer.
SEQ ID NO:65 is the PHM6726 forward external primer.
SEQ ID NO:66 is the PHM6726 forward internal primer.
SEQ ID NO:67 is the PHM6726 reverse internal primer.
SEQ ID NO:68 is the PHM6726 reverse external primer.
SEQ ID NO:69 is the PHM4910 forward external primer.
SEQ ID NO:70 is the PHM4910 forward internal primer.
SEQ ID NO:71 is the PHM4910 reverse internal primer.
SEQ ID NO:72 is the PHM4910 reverse external primer.
SEQ ID NO:73 is the PHM4598 forward external primer.
SEQ ID NO:74 is the PHM4598 forward internal primer.
SEQ ID NO:75 is the PHM4598 reverse internal primer.
SEQ ID NO:76 is the PHM4598 reverse external primer.
SEQ ID NO:77 is the PHM3507 forward external primer.
SEQ ID NO:78 is the PHM3507 forward internal primer.
SEQ ID NO:79 is the PHM3507 reverse internal primer.
SEQ ID NO:80 is the PHM3507 reverse external primer.
SEQ ID NO:81 is the PHM18292 forward external primer.
SEQ ID NO:82 is the PHM18292 forward internal primer.
SEQ ID NO:83 is the PHM18292 reverse internal primer.
SEQ ID NO:84 is the PHM18292 reverse external primer.
SEQ ID NO:85 is the PHM3004 forward external primer.
SEQ ID NO:86 is the PHM3004 forward internal primer.
SEQ ID NO:87 is the PHM3004 reverse internal primer.

SEQ ID NO:88 is the PHM3004 reverse external primer.
SEQ ID NO:89 is the PHM14122 forward external primer.
SEQ ID NO:90 is the PHM14122 forward internal primer.
SEQ ID NO:91 is the PHM14122 reverse internal primer.
SEQ ID NO:92 is the PHM14122 reverse external primer.
SEQ ID NO:93 is the PHM10270 forward external primer.
SEQ ID NO:94 is the PHM10270 forward internal primer.
SEQ ID NO:95 is the PHM10270 reverse internal primer.
SEQ ID NO:96 is the PHM10270 reverse external primer.
SEQ ID NO:97 is the PHM14092 forward external primer.
SEQ ID NO:98 is the PHM14092 forward internal primer.
SEQ ID NO:99 is the PHM14092 reverse internal primer.
SEQ ID NO:100 is the PHM14092 reverse external primer.
SEQ ID NO:101 is the reference sequence for marker PHM10028.
SEQ ID NO:102 is the reference sequence for marker PHM741.
SEQ ID NO:103 is the reference sequence for marker PHM6289.
SEQ ID NO:104 is the reference sequence for marker PHM13089.
SEQ ID NO:105 is the reference sequence for marker PHM2305.
SEQ ID NO:106 is the reference sequence for marker PHM9867.
SEQ ID NO:107 is the reference sequence for marker PHM7775.
SEQ ID NO:108 is the reference sequence for marker PHM16407.
SEQ ID NO:109 is the reference sequence for marker PHM14523.
SEQ ID NO:110 is the reference sequence for marker PHM2916.
SEQ ID NO: 11 is the reference sequence for marker PHM4583.
SEQ ID NO:112 is the PHM10028 forward external primer.
SEQ ID NO:113 is the PHM10028 forward internal primer.
SEQ ID NO:114 is the PHM10028 reverse internal primer.
SEQ ID NO:115 is the PHM10028 reverse external primer.
SEQ ID NO:116 is the PHM741 forward external primer.
SEQ ID NO:117 is the PHM741 forward internal primer.
SEQ ID NO:118 is the PHM741 reverse internal primer.
SEQ ID NO:119 is the PHM741 reverse external primer.
SEQ ID NO:120 is the PHM6289 forward external primer.
SEQ ID NO:121 is the PHM6289 forward internal primer.
SEQ ID NO:122 is the PHM6289 reverse internal primer.
SEQ ID NO:123 is the PHM6289 reverse external primer.
SEQ ID NO:124 is the PHM13089 forward external primer.
SEQ ID NO:125 is the PHM13089 forward internal primer.
SEQ ID NO:126 is the PHM13089 reverse internal primer.
SEQ ID NO:127 is the PHM13089 reverse external primer.
SEQ ID NO:128 is the PHM2305 forward external primer.
SEQ ID NO:129 is the PHM2305 forward internal primer.
SEQ ID NO:130 is the PHM2305 reverse internal primer.
SEQ ID NO:131 is the PHM2305 reverse external primer.
SEQ ID NO:132 is the PHM9867 forward external primer.
SEQ ID NO:133 is the PHM9867 forward internal primer.
SEQ ID NO:134 is the PHM9867 reverse internal primer.
SEQ ID NO:135 is the PHM9867 reverse external primer.
SEQ ID NO:136 is the PHM7775 forward external primer.
SEQ ID NO:137 is the PHM7775 forward internal primer.
SEQ ID NO:138 is the PHM7775 reverse internal primer.
SEQ ID NO:139 is the PHM7775 reverse external primer.
SEQ ID NO:140 is the PHM16407 forward external primer.
SEQ ID NO:141 is the PHM16407 forward internal primer.
SEQ ID NO:142 is the PHM16407 reverse internal primer.
SEQ ID NO:143 is the PHM16407 reverse external primer.
SEQ ID NO:144 is the PHM14523 forward external primer.
SEQ ID NO:145 is the PHM14523 forward internal primer.
SEQ ID NO:146 is the PHM14523 reverse internal primer.
SEQ ID NO:147 is the PHM14523 reverse external primer.
SEQ ID NO:148 is the PHM2916 forward external primer.
SEQ ID NO:149 is the PHM2916 forward internal primer.
SEQ ID NO:150 is the PHM2916 reverse internal primer.
SEQ ID NO:151 is the PHM2916 reverse external primer.
SEQ ID NO:152 is the PHM4583 forward external primer.
SEQ ID NO:153 is the PHM4583 forward internal primer.
SEQ ID NO:154 is the PHM4583 reverse internal primer.
SEQ ID NO:155 is the PHM4583 reverse external primer.
SEQ ID NO:156 is the reference sequence for marker PHM14165.
SEQ ID NO:157 is the reference sequence for marker PHM15960.
SEQ ID NO:158 is the reference sequence for marker PHM8438.
SEQ ID NO:159 is the reference sequence for marker PHM9867.
SEQ ID NO:160 is the reference sequence for marker PHM14523.
SEQ ID NO:161 is the PHM14165 forward external primer.
SEQ ID NO:162 is the PHM14165 forward internal primer.
SEQ ID NO:163 is the PHM14165 reverse internal primer.
SEQ ID NO:164 is the PHM14165 reverse external primer.
SEQ ID NO:165 is the PHM15960 forward external primer.
SEQ ID NO:166 is the PHM15960 forward internal primer.
SEQ ID NO:167 is the PHM15960 reverse internal primer.
SEQ ID NO:168 is the PHM15960 reverse external primer.
SEQ ID NO:169 is the PHM8438 forward external primer.
SEQ ID NO:170 is the PHM8438 forward internal primer.

SEQ ID NO:171 is the PHM8438 reverse internal primer.
SEQ ID NO:172 is the PHM8438 reverse external primer.
SEQ ID NO:173 is the PHM9867 forward external primer.
SEQ ID NO:174 is the PHM9867 forward internal primer.
SEQ ID NO:175 is the PHM9867 reverse internal primer.
SEQ ID NO:176 is the PHM9867 reverse external primer.
SEQ ID NO:177 is the PHM14523 forward external primer.
SEQ ID NO:178 is the PHM14523 forward internal primer.
SEQ ID NO:179 is the PHM14523 reverse internal primer.
SEQ ID NO:180 is the PHM14523 reverse external primer.

DETAILED DESCRIPTION

Grain moisture is an important trait for maize production. If the grain is too moist when the grower wants to harvest, then the grower may have to leave the crop in the field for a longer period of time, thereby exposing the crop to adverse weather and field conditions that could affect yield. Furthermore, once the grain is harvested, artificial drying may be needed to achieve a desired grain moisture level, requiring access to drying equipment, transportation to move the grain to the dryers, and power to run the dryers. Thus, it is desirable to identify and select maize plants with reduced grain moisture.

The present invention provides maize marker loci that demonstrate statistically significant co-segregation with grain moisture. Detection of these loci or additional linked loci can be used in marker assisted maize breeding programs to produce maize plants with reduced grain moisture.

The following definitions are provided as an aid to understand this invention.

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

The term "allele" refers to one of two or more different nucleotide sequences that occur at a specific locus.

"Allele frequency" refers to the frequency (proportion or percentage) at which an allele is present at a locus within an individual, within a line, or within a population of lines. For example, for an allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An "amplicon" is an amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to BACs and their propensities for coming together to form contiguous stretches of DNA. A BAC "assembles" to a contig based on sequence alignment, if the BAC is sequenced, or via the alignment of its BAC fingerprint to the fingerprints of other BACs. Public assemblies can be found using the Maize Genome Browser, which is publicly available on the internet.

An allele is "associated with" a trait when it is part of or linked to a DNA sequence or allele that affects the expression of the trait. The presence of the allele is an indicator of how the trait will be expressed.

A "BAC", or bacterial artificial chromosome, is a cloning vector derived from the naturally occurring F factor of *Escherichia coli*, which itself is a DNA element that can exist as a circular plasmid or can be integrated into the bacterial chromosome. BACs can accept large inserts of DNA sequence. In maize, a number of BACs each containing a large insert of maize genomic DNA from maize inbred line B73, have been assembled into contigs (overlapping contiguous genetic fragments, or "contiguous DNA"), and this assembly is available publicly on the internet.

A BAC fingerprint is a means of analyzing similarity between several DNA samples based upon the presence or absence of specific restriction sites (restriction sites being nucleotide sequences recognized by enzymes that cut or "restrict" the DNA). Two or more BAC samples are digested with the same set of restriction enzymes and the sizes of the fragments formed are compared, usually using gel separation.

"Backcrossing" refers to the process whereby hybrid progeny are repeatedly crossed back to one of the parents. In a backcrossing scheme, the "donor" parent refers to the parental plant with the desired gene/genes, locus/loci, or specific phenotype to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moleculaires Les Colloques, Vol. 72, pp. 45-56, and Openshaw et al., (1994) Marker-assisted Selection in Backcross Breeding, Analysis of Molecular Marker Data, pp. 41-43. The initial cross gives rise to the F1 generation; the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

A "chromosome" is a single piece of coiled DNA containing many genes that act and move as a unity during cell division and therefore can be said to be linked. It can also be referred to as a "linkage group".

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait (e.g., reduced grain moisture). Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

The term "complement" refers to a nucleotide sequence that is complementary to a given nucleotide sequence, i.e. the sequences are related by the Watson-Crick base-pairing rules.

The term "contiguous DNA" refers to an uninterrupted stretch of genomic DNA represented by partially overlapping pieces or contigs.

When referring to the relationship between two genetic elements, such as a genetic element contributing to grain moisture and a proximal marker, "coupling" phase linkage indicates the state where the "favorable" allele at the grain moisture locus is physically associated on the same chromosome strand as the "favorable" allele of the respective linked marker locus. In coupling phase, both favorable alleles are inherited together by progeny that inherit that chromosome strand.

The term "crossed" or "cross" refers to a sexual cross and involved the fusion of two haploid gametes via pollination to produce diploid progeny (e.g., cells, seeds or plants). The term encompasses both the pollination of one plant by another and selfing (or self-pollination, e.g., when the pollen and ovule are from the same plant).

A plant referred to herein as "diploid" has two sets (genomes) of chromosomes.

A plant referred to herein as a "doubled haploid" is developed by doubling the haploid set of chromosomes (i.e., half the normal number of chromosomes). A doubled haploid plant has two identical sets of chromosomes, and all loci are considered homozygous.

An "elite line" is any line that has resulted from breeding and selection for superior agronomic performance.

An "exotic maize strain" or an "exotic maize germplasm" is a strain derived from a maize plant not belonging to an available elite maize line or strain of germplasm. In the context of a cross between two maize plants or strains of germplasm, an exotic germplasm is not closely related by descent to the elite germplasm with which it is crossed. Most commonly, the exotic germplasm is not derived from any known elite line of maize, but rather is selected to introduce novel genetic elements (typically novel alleles) into a breeding program.

A "favorable allele" is the allele at a particular locus that confers, or contributes to, an agronomically desirable phenotype, e.g., reduced grain moisture, and that allows the identification of plants with that agronomically desirable phenotype. A favorable allele of a marker is a marker allele that segregates with the favorable phenotype.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or linkage groups) within a given species, generally depicted in a diagrammatic or tabular form. For each genetic map, distances between loci are measured by how frequently their alleles appear together in a population (their recombination frequencies). Alleles can be detected using DNA or protein markers, or observable phenotypes. A genetic map is a product of the mapping population, types of markers used, and the polymorphic potential of each marker between different populations. Genetic distances between loci can differ from one genetic map to another. However, information can be correlated from one map to another using common markers. One of ordinary skill in the art can use common marker positions to identify positions of markers and other loci of interest on each individual genetic map. The order of loci should not change between maps, although frequently there are small changes in marker orders due to e.g. markers detecting alternate duplicate loci in different populations, differences in statistical approaches used to order the markers, novel mutation or laboratory error.

A "genetic map location" is a location on a genetic map relative to surrounding genetic markers on the same linkage group where a specified marker can be found within a given species.

"Genetic mapping" is the process of defining the linkage relationships of loci through the use of genetic markers, populations segregating for the markers, and standard genetic principles of recombination frequency.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci. Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture, or more generally, all individuals within a species or for several species (e.g., maize germplasm collection or Andean germplasm collection). The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, that can be cultured into a whole plant.

"Grain moisture" is a property of grain that is measured in order to determine the optimal time to harvest. It can be measured using any of a number of methods, one of which is the use of a meter that measures the electrical properties of grain. While exact values for grain moisture can be obtained, grain moisture as used herein is a relative term. Thus, a plant with favorable alleles at either or both chromosome 9 QTL will have "reduced grain moisture" as compared to plants that do not have favorable alleles at these QTL.

A plant referred to as "haploid" has a single set (genome) of chromosomes.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to alleles at a particular locus, or to alleles at multiple loci along a chromosomal segment.

The term "heterogeneity" is used to indicate that individuals within the group differ in genotype at one or more specific loci.

The heterotic response of material, or "heterosis", can be defined by performance which exceeds the average of the parents (or high parent) when crossed to other dissimilar or unrelated groups.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (also referred to herein as "stiff stalk") and "Lancaster" or "Lancaster Sure Crop" (sometimes referred to as NSS, or non-Stiff Stalk).

Some heterotic groups possess the traits needed to be a female parent, and others, traits for a male parent. For example, in maize, yield results from public inbreds released from a population called BSSS (Iowa Stiff Stalk Synthetic population) has resulted in these inbreds and their derivatives becoming the female pool in the central Corn Belt. BSSS inbreds have been crossed with other inbreds, e.g. SD 105 and Maiz Amargo, and this general group of materials has become known as Stiff Stalk Synthetics (SSS) even though not all of the inbreds are derived from the original BSSS population (Mikel and Dudley (2006) *Crop Sci:* 46:1193-1205). By default, all other inbreds that combine well with the SSS inbreds have been assigned to the male pool, which for lack of a better name has been designated as NSS, i.e. Non-Stiff Stalk. This group includes several major heterotic groups such as Lancaster Surecrop, Iodent, and Leaming Corn.

An individual is "heterozygous" if more than one allele type is present at a given locus (e.g., a diploid individual with one copy each of two different alleles).

The term "homogeneity" indicates that members of a group have the same genotype at one or more specific loci.

An individual is "homozygous" if the individual has only one type of allele at a given locus (e.g., a diploid individual has a copy of the same allele at a locus for each of two homologous chromosomes).

The term "hybrid" refers to the progeny obtained between the crossing of at least two genetically dissimilar parents.

"Hybridization" or "nucleic acid hybridization" refers to the pairing of complementary RNA and DNA strands as well as the pairing of complementary DNA single strands.

The term "hybridize" means to form base pairs between complementary regions of nucleic acid strands.

An "IBM genetic map" can refer to any of following maps: IBM, IBM2, IBM2 neighbors, IBM2 FPC0507, IBM2 2004 neighbors, IBM2 2005 neighbors, IBM2 2005 neighbors frame, IBM2 2008 neighbors, IBM2 2008 neighbors frame, or the latest version on the maizeGDB website. IBM genetic maps are based on a B73×Mo17 population in which the progeny from the initial cross were random-mated for multiple generations prior to constructing recombinant inbred lines for mapping. Newer versions reflect the addition of genetic and BAC mapped loci as well as enhanced map refinement due to the incorporation of information obtained from other genetic maps or physical maps, cleaned date, or the use of new algorithms.

The term "inbred" refers to a line that has been bred for genetic homogeneity.

The term "indel" refers to an insertion or deletion, wherein one line may be referred to as having an inserted nucleotide or piece of DNA relative to a second line, or the second line may be referred to as having a deleted nucleotide or piece of DNA relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., detected by a marker that is associated with a phenotype, at a QTL, a transgene, or the like. In any case, offspring comprising the desired allele can be repeatedly backcrossed to a line having a desired genetic background and selected for the desired allele, to result in the allele becoming fixed in a selected genetic background. The process of "introgressing" is often referred to as "backcrossing" when the process is repeated two or more times.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

As used herein, the term "linkage" is used to describe the degree with which one marker locus is associated with another marker locus or some other locus. The linkage relationship between a molecular marker and a locus affecting a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM) of a single meiosis map (a genetic map based on a population that has undergone one round of meiosis, such as e.g. an $F_2$; the IBM2 maps consist of multiple meioses). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "in proximity to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

Linkage disequilibrium is most commonly assessed using the measure $r^2$, which is calculated using the formula described by Hill, W. G. and Robertson, A, Theor. Appl. Genet. 38:226-231(1968). When $r^2=1$, complete LD exists between the two marker loci, meaning that the markers have not been separated by recombination and have the same allele frequency. The $r^2$ value will be dependent on the population used. Values for $r^2$ above ⅓ indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome, e.g. where a nucleotide, gene, sequence, or marker is located.

The "logarithm of odds (LOD) value" or "LOD score" (Risch, Science 255:803-804 (1992)) is used in genetic interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage. LOD scores can also be used to show the strength of association between marker loci and quantitative traits in "quantitative trait loci" mapping. In this case, the LOD score's size is dependent on the closeness of the marker locus to the locus affecting the quantitative trait, as well as the size of the quantitative trait effect.

"Maize" refers to a plant of the *Zea mays* L. ssp. *mays* and is also known as "corn".

The term "maize plant" includes whole maize plants, maize plant cells, maize plant protoplast, maize plant cell or maize tissue culture from which maize plants can be regenerated, maize plant calli, maize plant clumps and maize plant cells that are intact in maize plants or parts of maize plants, such as maize seeds, maize cobs, maize flowers, maize cotyledons, maize leaves, maize stems, maize buds, maize roots, maize root tips and the like.

A "marker" is a means of finding a position on a genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA). Depending on the DNA marker technology, the marker will consist of complementary primers flanking the locus and/or complementary probes that hybridize to polymorphic alleles at the locus. A DNA marker, or a genetic marker, can also be used to describe the gene, DNA sequence or nucleotide on the chromosome itself (rather than the components used to detect the gene or DNA sequence) and is often used when that DNA marker is associated with a particular trait in human genetics (e.g. a marker for breast cancer). The term marker locus is the locus (gene, sequence or nucleotide) that the marker detects.

Markers that detect genetic polymorphisms between members of a population are well-established in the art. Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected e.g. via DNA sequencing, PCR-based sequence specific amplification methods, detection of polynucleotide polymorphisms by allele specific hybridization (ASH), dynamic allele-specific hybridization (DASH), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology has the advantage of being able to detect a series of linked SNP alleles that constitute a haplotype. Haplotypes tend to be more informative (detect a higher level of polymorphism) than SNPs.

A "marker allele", alternatively an "allele of a marker locus", can refer to one of a plurality of polymorphic nucleotide sequences found at a marker locus in a population.

"Marker assisted selection" (of MAS) is a process by which individual plants are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus.

A "marker locus" is a specific chromosome location in the genome of a species where a specific marker can be found. A marker locus can be used to track the presence of a second linked locus, e.g., one that affects the expression of a phenotypic trait. For example, a marker locus can be used to monitor segregation of alleles at a genetically or physically linked locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "phenotype", "phenotypic trait", or "trait" can refer to the observable expression of a gene or series of genes. The phenotype can be observable to the naked eye, or by any other means of evaluation known in the art, e.g., weighing, counting, measuring (length, width, angles, etc.), microscopy, biochemical analysis, or an electromechanical assay. In some cases, a phenotype is directly controlled by a single gene or genetic locus, i.e., a "single gene trait" or a "simply inherited trait". In the absence of large levels of environmental variation, single gene traits can segregate in a population to give a "qualitative" or "discrete" distribution, i.e. the phenotype falls into discrete classes. In other cases, a phenotype is the result of several genes and can be considered a "multigenic trait" or a "complex trait". Multigenic traits segregate in a population to give a "quantitative" or "continuous" distribution, i.e. the phenotype cannot be separated into discrete classes. Both single gene and multigenic traits can be affected by the environment in which they are being expressed, but multigenic traits tend to have a larger environmental component.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A maize plant "derived from an inbred in the Stiff Stalk Synthetic population" may be a hybrid.

A "polymorphism" is a variation in the DNA between two or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel".

An allele "positively" correlates with a trait when it is linked to it and when presence of the allele is an indicator that the desired trait or trait form will occur in a plant comprising the allele.

The "probability value" or "p-value" is the statistical likelihood that the particular combination of a phenotype and the presence or absence of a particular marker allele is random. Thus, the lower the probability score, the greater the likelihood that a locus and a phenotype are associated. The probability score can be affected by the proximity of the first locus (usually a marker locus) and the locus affecting the phenotype, plus the magnitude of the phenotypic effect (the change in phenotype caused by an allele substitution). In some aspects, the probability score is considered "significant" or "nonsignificant". In some embodiments, a probability score of 0.05 (p=0.05, or a 5% probability) of random assortment is considered a significant indication of association. However, an acceptable probability can be any probability of less than 50% (p=0.5). For example, a significant probability can be less than 0.25, less than 0.20, less than 0.15, less than 0.1, less than 0.05, less than 0.01, or less than 0.001.

A "production marker" or "production SNP marker" is a marker that has been developed for high-throughput purposes. Production SNP markers are developed to detect specific polymorphisms and are designed for use with a variety of chemistries and platforms. The marker names used here begin with a PHM prefix to denote 'Pioneer Hi-Bred Marker', followed by a number that is specific to the sequence from which it was designed, followed by a "." or a "-" and then a suffix that is specific to the DNA polymorphism. A marker version can also follow (A, B, C etc.) that denotes the version of the marker designed to that specific polymorphism.

The term "progeny" refers to the offspring generated from a cross.

A "progeny plant" is a plant generated from a cross between two plants.

The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question. An "allele of a QTL" can comprise multiple genes or other genetic factors within a contiguous genomic region or linkage group, such as a haplotype. An allele of a QTL can denote a haplotype within a specified window wherein said window is a contiguous genomic region that can be defined, and tracked, with a set of one or more polymorphic markers. A haplotype can be defined by the unique fingerprint of alleles at each marker within the specified window.

A "reference sequence" or a "consensus sequence" is a defined sequence used as a basis for sequence comparison. The reference sequence for a PHM marker is obtained by sequencing a number of lines at the locus, aligning the nucleotide sequences in a sequence alignment program (e.g. Sequencher), and then obtaining the most common nucleotide sequence of the alignment. Polymorphisms found among the individual sequences are annotated within the consensus sequence. A reference sequence is not usually an exact copy of any individual DNA sequence, but represents an amalgam of available sequences and is useful for designing primers and probes to polymorphisms within the sequence.

In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

A "topcross test" is a test performed by crossing each individual (e.g. a selection, inbred line, clone or progeny individual) with the same pollen parent or "tester", usually a homozygous line.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances. Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C., depending on primer length. Additional guidelines for determining hybridization parameters are provided in numerous references.

An "unfavorable allele" of a marker is a marker allele that segregates with the unfavorable plant phenotype, therefore providing the benefit of identifying plants that can be removed from a breeding program or planting.

The term "yield" refers to the productivity per unit area of a particular plant product of commercial value. For example, yield of maize is commonly measured in bushels of seed per acre or metric tons of seed per hectare per season. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

Sequence alignments and percent identity calculations may be determined using a variety of comparison methods designed to detect homologous sequences including, but not limited to, the MEGALIGN® program of the LASER-GENE® bioinformatics computing suite (DNASTAR® Inc., Madison, Wis.). Unless stated otherwise, multiple alignment of the sequences provided herein were performed using the Clustal V method of alignment (Higgins and Sharp, CABIOS. 5:151 153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

Genetic Mapping

It has been recognized for quite some time that specific genetic loci correlating with particular phenotypes, such as grain moisture, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods well known in the art are available for detecting molecular markers or clusters of molecular markers that co-segregate with a trait of interest, such as grain moisture. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) Population-based association analysis and 2) Traditional linkage analysis. In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, Genetics 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

The present invention provides maize marker loci that demonstrate statistically significant co-segregation with grain moisture, as determined by traditional linkage analysis and by whole genome association analysis. Detection of these loci or additional linked loci can be used in marker assisted maize breeding programs to produce plants with reduced grain moisture.

Activities in marker assisted maize breeding programs may include but are not limited to: selecting among new breeding populations to identify which population has the highest frequency of favorable nucleic acid sequences based on historical genotype and agronomic trait associations, selecting favorable nucleic acid sequences among progeny in breeding populations, selecting among parental lines based on prediction of progeny performance, and advancing lines in germplasm improvement activities based on presence of favorable nucleic acid sequences.

QTL Locations

Two QTL on chromosome 9 were identified from a linkage mapping analysis (Example 1). The first QTL, identified herein as QTL9-1, is located at 72-79 cM on a single meiosis map (e.g. the PHB map), which approximately corresponds to 200.4-230.6 cM on an IBM2 map, the most recent version of which is the IBM2 2008 map. QTL9-1 was found to be associated with both grain moisture and yield. The second QTL, identified herein as QTL9-2, is located at 93-98 cM on a single meiosis map (e.g. the PHB map), which approximately corresponds to 317-323 cM on an IBM2 map, the most recent version of which is the IBM2 2008 map. QTL9-2 was found to be associated with grain moisture. These QTL were further validated by a whole genome association analysis.

Chromosomal Intervals

Chromosomal intervals that correlate with grain moisture are provided. A variety of methods well known in the art are available for identifying chromosomal intervals. The boundaries of such chromosomal intervals are drawn to encompass markers that will be linked to the gene(s) controlling the trait of interest. In other words, the chromosomal interval is drawn such that any marker that lies within that interval (including the terminal markers that define the boundaries of the interval) can be used as a marker for grain moisture. Tables 1 and 2 show markers within the QTL9-1 and QTL9-2 regions, respectively, that are shown herein to associate with grain moisture and that are linked to a gene(s) controlling grain moisture. Reference sequences for each of the PHM markers listed in Tables 1 and 2 are represented by SEQ ID NOs:1-20 and the primers are represented by SEQ ID NOs:21-100.

TABLE 1

QTL9-1 Markers

| Marker | PHB Map Position | IBM2 Map Position | B73 BAC(s) on which marker is located | Position in most recent B73 assembly | internal contig |
|---|---|---|---|---|---|
| PHM18206 | 71.5 | N/A | c0152O14 | 24,337,082-24,385,520 | 9004 |
| PHM6567 | 75.2 | 220.7 | c0412K22 | 28,512,451-28,460,814 | 9004 |
| PHM4691 | 75.3 | 220.1 | b0428G16 | 28,901,175-28,901,074 | 9004 |
| PHM229 | 74.0 | 220.1 | c0202D12 | 30,129,229-30,129,128 | 9005 |
| PHM9929 | 75.8 | 226.3 | c0504I01; | 43,460,951-43,460,850; | 9007 |

TABLE 1-continued

QTL9-1 Markers

| Marker | PHB Map Position | IBM2 Map Position | B73 BAC(s) on which marker is located | Position in most recent B73 assembly | internal contig |
|---|---|---|---|---|---|
| PHM3159 | 77.0 | 226.3* | b0605B16 b0131J16 | 44,264,873-44,264,772 44,384,523-44,350,417 | 9007 |
| PHM15758 | 76.1 | 226.3 | c0245O02 | 47,163,201-47,223,179 | 9008 |
| PHM5208 | 75.9 | 226.3* | N/A | N/A | 9011 |
| PHM6667 | 76.2 | 226.3 | c0242C10 | 60,969,688-60,966,572 | 9011 |
| PHM17246 | 77.0 | 226.3 | b0631G11 | 62,629,552-62,629,451 | 9011 |
| PHM14370 | 76.9 | 226.3 | c0150K08 | N/A | 9011 |
| PHM6726 | 77.3 | 230.6 | c0194F10 | 84,272,694-84,399,377 | 9013 |
| PHM4910 | 78.8 | 230.6 | c0131H04; c0009L19 | 89,601,648-89,601,547; 89,745,216-89,854,317 | 9013 |

*Map position is estimated based on relative physical map position.

TABLE 2

QTL9-2 Markers

| Marker | PHB Map Position | IBM2 Map Position | B73 BAC(s) on which marker is located | Position in most recent B73 assembly | Internal contig |
|---|---|---|---|---|---|
| PHM4598 | 94.5 | 317.0* | b0321m22 | 123,407,712-123,456.512 | 9018 |
| PHM3507 | 94.6 | 317.0 | b0321m22 | 123,407,712-123,456.512 | 9018 |
| PHM18292 | 94.4 | 317.0 | b0377g24 | 124,131,940-124,131,839 | 9018 |
| PHM3004 | 94.7 | 317.0 | c0062B12; b0377G24 | 124,178,372-124,254,793: 124,131,940-124,131,839 | 9018 |
| PHM14122 | 97.0 | 320.6 | c0286K12 | 126,975,669-127,011,266 | 9018 |
| PHM10270 | 97.5 | 322.6 | b0594A18 | 127,451,022-127,545,826 | 9018 |
| PHM14092 | 97.8 | 322.6 | c0286G14 | 128.070,700-128,070,599 | 9018 |

*Map position is estimated based on relative physical map position.

Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identify the same QTL or two different QTL. Regardless, knowledge of how many QTL are in a particular interval is not necessary to make or practice the invention.

The intervals described below encompass markers that co-segregate with grain moisture. The clustering of markers that co-segregate with grain moisture within a localized region occurs in relatively small domains on the chromosomes, indicating the presence of one or more QTL in those chromosome regions. The interval was drawn to encompass markers that co-segregate with grain moisture. The intervals are defined by the markers on their termini, where the interval encompasses markers that map within the interval as well as the markers that define the termini. An interval described by the terminal markers that define the endpoints of the interval will include the terminal markers and any marker localizing within that chromosomal domain, whether those markers are currently known or unknown.

The QTL9-1 interval may encompass any of the markers identified herein as being associated with the grain moisture trait including: PHM18206, PHM9929, PHM6726, PHM4910, PHM6667, PHM229, PHM6567, PHM5208, PHM15758, PHM14370, PHM3159, PHM17246, and PHM4691. The QTL9-1 interval, for example, may be defined by markers PHM18206 and PHM4910, which are separated by the greatest distance on the physical map, wherein the interval encompasses that markers that map within the interval as well as markers PHM18206 and PHM4910. Any marker located within these intervals can find use as a marker for grain moisture and can be used in the context of the methods presented herein to identify and/or select maize plants that have reduced grain moisture.

The QTL9-2 interval may encompass any of the markers identified herein as being associated with the grain moisture trait including: PHM18292, PHM4598, PHM3507, PHM3004, PHM14122, PHM10270, and PHM14092. The QTL9-2 interval, for example, may be defined by markers PHM4598 and PHM14092, which are separated by the greatest distance on the physical map, wherein the interval encompasses that markers that map within the interval as well as markers PHM4598 and PHM14092. Any marker located within these intervals can find use as a marker for grain moisture and can be used in the context of the methods presented herein to identify and/or select maize plants that have reduced grain moisture.

Chromosomal intervals can also be defined by markers that are linked to (show linkage disequilibrium with) a QTL marker, and $r^2$ is a common measure of linkage disequilibrium (LD) in the context of association studies. If the $r^2$ value of LD between a chromosome 9 marker locus lying within either of the QTL9-1 or QTL9-2 intervals, for example, and another chromosome 9 marker locus in close proximity is greater than ⅓ (Ardlie et al., Nature Reviews Genetics 3:299-309 (2002)), the loci are in linkage disequilibrium with one another.

Markers and Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can co-segregate with grain moisture, it is important to note that the marker locus is not necessarily responsible for the expression of the grain moisture phenotype. For example, it is not a requirement that the marker polynucleotide sequence be part of a gene that is responsible for the grain moisture phenotype (for example, is part of the gene open reading frame). The association between a specific marker allele and reduced grain moisture is due to the original "coupling" linkage phase between the marker allele and the allele in the ancestral maize line from which the allele originated. Eventually, with repeated recombination, crossing over events between the marker and genetic locus can change this orientation. For this reason, the favorable marker allele may change depending on the linkage phase that exists within the parent having reduced grain moisture that is used to create segregating populations. This does not change the fact that the marker can be used to monitor segregation of the phenotype. It only changes which marker allele is considered favorable in a given segregating population.

Methods presented herein include detecting the presence of one or more marker alleles associated with reduced grain moisture in a maize plant and then identifying and/or selecting maize plants that have favorable alleles at those marker loci. Markers listed in Tables 1 and 2 have been identified herein as being associated with grain moisture and hence can be used to predict grain moisture in a maize plant. Any marker within 50 cM, 40 cM, 30 cM, 20 cM, 15 cM, 10 cM, 9 cM, 8 cM, 7 cM, 6 cM, 5 cM, 4 cM, 3 cM, 2 cM, 1 cM, 0.75 cM, 0.5 cM or 0.25 cM of any of the markers in Tables 1 and 2 could also be used to predict grain moisture in a maize plant.

Marker Assisted Selection

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the maize genome containing increasing densities of public maize markers has facilitated maize genetic mapping and MAS. See, e.g. the IBM2 Neighbors maps, which are available online on the MaizeGDB website.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics,* 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide.* Academic press. pp 75-135).

Various types of SSR markers can be generated, and SSR profiles can be obtained by gel electrophoresis of the amplification products. Scoring of marker genotype is based on the size of the amplified fragment. An SSR service for maize is available to the public on a contractual basis by DNA Landmarks in Saint-Jean-sur-Richelieu, Quebec, Canada.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; and Bhattramakki and Rafalski (2001) Discovery and application of single nucleotide polymorphism markers in plants. In: R. J. Henry, Ed, *Plant Genotyping: The DNA Fingerprinting of Plants,* CABI Publishing, Wallingford. A wide range of commercially available technologies utilize these and other methods to interrogate SNPs including Masscode™ (Qiagen), Invader®. (Third Wave Technologies) and Invader Plus®, SnapShot®. (Applied Biosystems), Taqman®. (Applied Biosystems) and Beadarrays®. (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), *Plant Science* 162:329-333). Haplotypes can be more informative than single SNPs and can be more descriptive of any particular genotype. For example, a single SNP may be allele 'T' for a specific line or variety with reduced grain moisture, but the allele 'T' might also occur in the maize breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

Many of the PHM markers presented herein can readily be used as FLP markers to select for the gene loci on chromosome 9, owing to the presence of insertions/deletion polymorphisms. Primers for the PHM markers can also be used to convert these markers to SNP or other structurally similar or functionally equivalent markers (SSRs, CAPs, indels, etc.), in the same regions. One very productive approach for SNP conversion is described by Rafalski (2002a) *Current opinion in plant biology* 5 (2): 94-100 and also Rafalski (2002b) *Plant Science* 162: 329-333. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically with respect to the fine map information described herein, one can readily use the information provided herein to obtain additional polymorphic SNPs (and other markers) within the region amplified by the primers listed in this disclosure. Markers within the described map region can be hybridized to BACs or other genomic libraries, or electronically aligned with genome sequences, to find new sequences in the same approximate location as the described markers.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the maize species, or even across other species that have been genetically or physically aligned with maize, such as rice, wheat, barley or sorghum.

In general, MAS uses polymorphic markers that have been identified as having a significant likelihood of cosegregation with a phenotype, such as grain moisture. Such markers are presumed to map near a gene or genes that give the plant its grain moisture phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny. Thus, plants with reduced grain moisture can be selected for by detecting one or more marker alleles, and in addition, progeny plants derived from those plants can also be selected. Hence, a plant containing a desired genotype in a given chromosomal region (i.e. a genotype associated with reduced grain moisture) is obtained and then crossed to another plant. The progeny of such a cross would then be evaluated genotypically using one or more markers and the progeny plants with the same genotype in a given chromosomal region would then be selected as having reduced grain moisture.

PHM markers were identified from both linkage mapping and association analysis as being associated with grain moisture in Stiff Stalk Synthetic populations. Reference sequences for each of the PHM markers are represented by SEQ ID NOs:1-20 and the primers for the PHM marker loci are represented by SEQ ID NOs:21-100. For PHM marker analysis, nested PCR reactions can be performed, using the external and internal primers for each PHM marker. In the first PCR reaction, 0.90 µl of 10×PCR buffer, 0.18 µl of 10 mM dNTP mix, 0.27 µl of 50 mM MgCl$_2$, 1.50 µl of 2.5 µM external forward primer, 1.50 µl of 2.5 µM external reverse primer, 0.04 µl of Platinum Taq, 1.61 µl of ddH2O, and 3 µl of 1.5 ng/µl DNA are used. The thermocycling conditions constitute: 95° C. at 5 minutes; 94° C. for 20 seconds, 55° C. for 30 seconds, and 72° C. for 2 minutes, repeated for 24 cycles; 72° C. for 10 minutes; and a hold at 4° C. The DNA produced from the first round of PCR is then diluted 1:9 with TE for use in the second round of PCR. The reaction mix for the second round of PCR is the same except the internal sets of primers are used, and the DNA is the diluted DNA from the first round of PCR. The thermocycling conditions for the second round of PCR constitute: 95° C. at 5 minutes; 94° C. for 20 seconds, 55° C. for 30 seconds, and 72° C. for 2 minutes, repeated for 28 cycles; 72° C. for 10 minutes; and a hold at 4° C. The PCR products are then sequenced directly.

PCR products can be sequenced directly in one or both directions, and the resulting sequences can be aligned and polymorphisms can be identified. The polymorphisms are not limited to single nucleotide polymorphisms (SNPs), but also include indels, CAPS, SSRs, and VNTRs (variable number of tandem repeats).

SNPs identified within the PHM marker sequences that are associated with grain moisture are presented herein including: PHM18206-5, PHM9929-8, PHM6726-10, PHM4910-5, PHM6667-11, PHM229-15, PHM6567-10, PHM5208-11, PHM15758-6, PHM14370-9, PHM3159-14, PHM17246-16, PHM4691-9, PHM10270-13, PHM4598-22, PHM14092-77, PHM18292-9, PHM3507-13, PHM3004-13, and PHM14122-22. The marker names begin with a PHM prefix to denote 'Pioneer Hi-Bred Marker', followed by a number that is specific to the sequence from which it was designed, followed by a "." or a "-" and then a numeric suffix that is specific to the DNA polymorphism.

Tables 8 and 9 list SNP markers and the corresponding favorable alleles that could be used in marker assisted selection to identify and select the favorable QTL alleles (the alleles associated with reduced grain moisture) at QTL9-1 and QTL9-2, respectively, in a maize plant. The maize plant may be an inbred in the Stiff Stalk Synthetic population or may be derived from an inbred in the Stiff Stalk Synthetic population.

The SNP markers could be used alone or in combination (i.e. a SNP haplotype) to select for favorable QTL alleles associated with reduced grain moisture. For example, a SNP haplotype at QTL9-1 can comprise: a "T" at PHM9929-8, a "T" at PHM6667-11, a "C" at PHM229-15, a "T" at PHM6567-10, a "T" at PHM5208-11, a "C" at PHM15758-6, a "G" at PHM14370-9, a "C" at PHM3159-14, and a "T" at PHM17246-16, or any combination thereof; and a SNP haplotype at QTL9-2 can comprise: a "C" at PHM10270-13, a "C" at PHM4598-22, a "C" at PHM14092-77, an "A" at PHM18292-9, a "G" or an "A" at PHM3507-13, a "G" at PHM3004-13, and a "G" at PHM14122-22, or any combination thereof.

The skilled artisan would expect that there might be additional polymorphic sites at marker loci in and around the chromosome 9 markers identified herein, wherein one or more polymorphic sites is in linkage disequilibrium (LD) with an allele at one or more of the polymorphic sites in the haplotype and thus could be used in a marker assisted selection program to introgress a QTL allele of interest. Two particular alleles at different polymorphic sites are said to be in LD if the presence of the allele at one of the sites tends to predict the presence of the allele at the other site on the same chromosome (Stevens, *Mol. Diag.* 4:309-17 (1999)). The marker loci can be located within 5 cM, 2 cM, or 1 cM of the grain moisture QTL.

The skilled artisan would understand that allelic frequency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

Plant Compositions

Maize plants identified and/or selected by any of the methods described above are also of interest. This includes any plant from the species *Zea mays* that has within its genome a haplotype at QTL9-1 consisting of: a "T" at PHM9929-8, a "T" at PHM6667-11, a "C" at PHM229-15, a "T" at PHM6567-10, a "T" at PHM5208-11, a "C" at PHM15758-6, a "G" at PHM14370-9, a "C" at PHM3159-14, and that exhibits reduced grain moisture when compared to a maize plant that does not have the haplotype in its genome. This also includes any maize plant that has within its genome a haplotype at QTL9-2 consisting of: a "C" at PHM10270-13, a "C" at PHM4598-22, a "C" at PHM14092-77, an "A" at PHM18292-9, a "G" or an "A" at PHM3507-13, a "G" at PHM3004-13, and a "G" at PHM14122-22; and that exhibits reduced grain moisture and no decrease in yield when compared to a maize plant that does not have the haplotype in its genome. The maize plant may be an inbred in the Stiff Stalk Synthetic population or may be a progeny plant derived from a Stiff Stalk Synthetic population.

Transgenics

Preferred haplotypes and QTL identified by the present disclosure may be advanced as candidate genes for inclusion in expression constructs, i.e., transgenes. Nucleic acids underlying haplotypes or QTL of interest may be expressed in plant cells by operably linking them to a promoter functional in plants. Nucleic acids underlying haplotypes or QTL of interest may have their expression modified by double-stranded RNA-mediated gene suppression, also known as RNA interference ("RNAi"), which includes suppression mediated by small interfering RNAs ("siRNA"), trans-acting small interfering RNAs ("ta-siRNA"), or micro-RNAs ("miRNA").

Methods are known in the art for assembling and introducing constructs into a cell in such a manner that the nucleic acid molecule for a trait is transcribed into a functional mRNA molecule that is translated and expressed as a protein product.

Seed Treatments

To protect and to enhance yield production and trait technologies, seed treatment options can provide additional crop plan flexibility and cost effective control against insects, weeds and diseases, thereby further enhancing the invention described herein. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematicides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *bacillus* spp. (including one or more of *cereus, firmus, megaterium, pumilis, sphaericus, subtilis* and/or *thuringiensis*), *bradyrhizobium* spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluquinconazole, flurazole, fluxofenim, harpin protein, imazalil, imidacloprid, ipconazole, isoflavenoids, lipochitooligosaccharide, mancozeb, manganese, maneb, mefenoxam, metalaxyl, metconazole, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA registration number 00293500419, containing quintozen and terrazole. TCMTB refers to 2-(thiocyanomethylthio)benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Example 1

Mapping of a Grain Moisture QTL on Chromosome 9 in a Maize Stiff Stalk Synthetic Population Observations in Breeding Populations Breeding populations are generated by crossing high value inbreds from within heterotic groupings for the purposes of generating the next generation of newly improved elite inbreds. The populations are tested across multiple locations for agronomic traits of interest to the breeder. When the same populations are marker profiled, QTLs can be mapped using such methods as regression or maximum likelihood.

Over several years (2003-2008), phenotypic and marker data were collected on breeding populations leading to an observation of a strong genetic signal in the region 60 to 100 cM (distances are based on a single meiosis map) on chromosome 9. The signal correlated with moisture and other agronomic traits in Stiff Stalk Synthetic (SSS) maize populations, in particular, in mid-US maturities. The strong signal warranted further investigation via populations specifically developed for more detailed, or 'fine', mapping of the QTL in this region.

Population Development for Fine Mapping

A biparental backcross-derived Stiff Stalk Synthetic (SSS) population was created from a cross between inbred PHCA5 and inbred PH705, and the resulting $F_1$ progeny were crossed again to PH705. Another round of backcrossing to PH705 was subsequently performed, creating $BC_2$ lines which were then selfed over several generations, with individual ear selections being made at each generation. At the $BC_2F_3$ stage, 1700 lines were genotyped with nine SNP markers that were designed to detect recombinations occurring within the 57.5 cM to 97.5 cM region on chromosome 9. These 9 SNP markers were PHM10028-12, PHM18206-5, PHM9929-8, PHM6726-10, PHM4910-5, PHM741-38, PHM6289-369, PHM13089-15 and PHM10270-13 and are described in Table 3. The markers were designed for use with Invader Plus® reagents which are proprietary to Third Wave Technologies (Madison, Wis., USA). $BC_2F_3$ lines containing recombinations within the targeted region were further selected for selfing. Some additional lines that were non-recombinants within the region were also selected as controls. The resulting $BC_2F_4$ lines were crossed with inbred PHCND. PHCND is classified as a member of the non-Stiff Stalk (NSS) heterotic group; thus, the stiff-stalk $BC_2F_4$ lines crossed with PHCND generated hybrids, or test-crosses, for which grain moisture could be assessed. During the crossing procedure, the SNP markers were used to select individual $BC_2F_4$ plants with homozygous fixed recombinants, and following crossing with PHCND, only ears from the homozygous recombinant plants were harvested resulting in 336 $BC_2F_4$ lines. This seed formed the basis of the field experiments in 2009.

The $BC_2F_4$ lines were selfed to generate 220 $BC_2F_5$ lines that were further crossed to the non-Stiff Stalk inbred PHVAM to generate hybrid test-crosses materials for evaluation in 2010 experiments.

2009 Field Evaluations

In 2009, the 336 test-cross entries (generated from $BC_2F_4$ PHCA5×PH705 recombinants crossed with PHCND) were evaluated for grain moisture and yield. The entries were planted in four yield test locations consisting of two-row test plots per entry that were combine harvested. Two locations were in Princeton, Ill.; one in Marion, Iowa; and one in Windfall, Ind. As agronomic controls within each experiment, 20% of the entries were replicated at each location (experimental design is described in Williams et al. 2011. *Biometrical Journal* 1:19-27). Six replicates of parental test-cross entries were also added as controls at each of the 4 locations; the parental test-cross entries consisted of the parental inbreds PH705 and PHCA5 being crossed to PHCND to generate hybrid materials. Yield was measured in bushels acre$^{-1}$ and grain moisture was measured at harvest using a calibrated electronic moisture meter.

2010 Field Evaluations

In 2010, the hybrid test-cross materials generated by crossing the PHCA5×PH705 $BC_2F_5$ population to PHVAM were evaluated for yield and grain moisture in four yield test locations: two in Windfall, Ind. and two in Princeton, Ill. A series of 144 overlapping $BC_2F_5$ test-cross entries were selected to be grown at each location and approximately 20% of the selected entries were replicated in each experiment as agronomic controls. Eleven replicates of parental test-cross entries were also added as controls which consisted of the parental inbreds PH705 and PHCA5 being crossed to PHVAM to generate hybrid materials. Yield was measured in bushels acre$^{-1}$ and grain moisture was measured at harvest using a calibrated electronic moisture meter.

QTL Analysis Based on 2009 and 2010 Data

A spatial mixed linear model (Gilmour (1997) *Journal of Agricultural, Biological and Environmental Statistics* 2:269-293; Cullis (2006) *Journal of Agricultural, Biological and Environmental Statistics* 11:381) was fit to the field data as a base model for a likelihood ratio test (LRT). The base model fit a fixed effect for locations, random effects for ear group, entries within ear group, interactions of location with these two random effects, random effects for row and column at each location, and a first order separable autoregressive process (AR1×AR1) at each location (Gogel (1997) *Spatial Analysis of multi-environment variety trials*; Cullis et al. (1998) Biometrics 54:1-18). Markers listed in Tables 3 and 4 were utilized for mapping. Each marker was added one at a time to the base model, and a LRT statistic was calculated and plotted against the cM position of the marker being tested (FIG. 1). QTL were considered significant at an LRT threshold of 13.81; equivalent to a LOD of 3.

TABLE 3

Markers Used for Selection of Recombinants and Genotyping in 2009 and 2010 Experiments and for Mapping

| Marker | Reference Sequence | Primer Sequences | SNP identifier | SNP Position in Reference Sequence | PHCA5 allele | PH705 allele | PHB Map Position* |
|---|---|---|---|---|---|---|---|
| PHM10028 | SEQ ID NO: 101 | SEQ ID NOs: 112-115 | PHM10028-12 | 367 | C | T | 57.5 |
| PHM18206 | SEQ ID NO: 1 | SEQ ID NOs: 21-24 | PHM18206-5 | 334 | T | C | 71.5 |

TABLE 3-continued

Markers Used for Selection of Recombinants and Genotyping in 2009 and 2010 Experiments and for Mapping

| Marker | Reference Sequence | Primer Sequences | SNP identifier | SNP Position in Reference Sequence | PHCA5 allele | PH705 allele | PHB Map Position* |
|---|---|---|---|---|---|---|---|
| PHM9929 | SEQ ID NO: 5 | SEQ ID NOs: 37-40 | PHM9929-8 | 163 | T | A | 75.8 |
| PHM6726 | SEQ ID NO: 12 | SEQ ID NOs: 65-68 | PHM6726-10 | 397 | A | T | 77.3 |
| PHM4910 | SEQ ID NO: 13 | SEQ ID NOs: 69-72 | PHM4910-5 | 212 | G | A | 78.8 |
| PHM741 | SEQ ID NO: 102 | SEQ ID NOs: 116-119 | PHM741-38 | 277 | T | C | 79.4 |
| PHM6289 | SEQ ID NO: 103 | SEQ ID NOs: 120-123 | PHM6289-369 | 190 | T | C | 80.8 |
| PHM13089 | SEQ ID NO: 104 | SEQ ID NOs: 124-127 | PHM13089-15 | 263 | G | A | 83.2 |
| PHM10270 | SEQ ID NO: 19 | SEQ ID NOs: 93-96 | PHM10270-13 | 260 | T | C | 97.5 |

*The PHB map represents a single meiosis map.

TABLE 4

Additional Markers Used for Mapping

| Marker | Reference Sequence | Primer Sequences | SNP identifier | SNP Position in Reference Sequence | PHCA5 allele | PH705 allele | PHB Map Position* |
|---|---|---|---|---|---|---|---|
| PHM2305 | SEQ ID NO: 105 | SEQ ID NOs: 128-131 | PHM2305-17 | 452 | T | C | 67.3 |
| PHM6667 | SEQ ID NO: 9 | SEQ ID NOs: 53-56 | PHNA6667-11 | 237 | T | C | 76.2 |
| PHM9867 | SEQ ID NO: 106 | SEQ ID NOs: 132-135 | PHM9867-22 | 355 | T | G | 80.6 |
| PHM7775 | SEQ ID NO: 107 | SEQ ID NOs: 136-139 | PHM7775-65 | 387 | A | G | 81.5 |
| PHM16407 | SEQ ID NO: 108 | SEQ ID NOs: 140-143 | PHM16407-19 | 186 | A | G | 82.6 |
| PHM14523 | SEQ ID NO: 109 | SEQ ID NOs: 144-147 | PHM14523-8 | 342 | C | G | 85.0 |
| PHM2916 | SEQ ID NO: 110 | SEQ ID NOs: 148-151 | PHM2916-18 | 245 | G | T | 92.5 |
| PHM4583 | SEQ ID NO: 111 | SEQ ID NOs: 152-155 | PHM4583-7 | 314 | C | T | 93.0 |
| PHM4598 | SEQ ID NO: 14 | SEQ ID NOs: 73-76 | PHM4598-22 | 246 | G | C | 94.5 |
| PHM14092 | SEQ ID NO: 20 | SEQ ID NOs: 97-100 | PHM14092-77 | 253 | G | C | 97.8 |

*The PHB map represents a single meiosis map

Prominent QTL (QTL on chromosome 9 location 1, or QTL 9-1) were identified for both grain moisture and yield between 71.7 and 79.0 cM on chromosome 9. The location range for QTL9-1 is based on 99% confidence intervals (CI) calculated for each year of data by a method which approximates the QTL distribution based on the LRT (Li, H. (2011) *Journal of Genetics* 90(2):355-360) (Table 5). Nearly identical QTL positions were identified in 2009 and in 2010, with the most likely position for both the grain moisture and yield QTLs being located at 75.8 cM in 2009, and at 77.3 and 76.2 cM for moisture and yield, respectively, in 2010 (Table 5). A second smaller QTL (QTL 9-2) for moisture was also apparent within the region 93.4-97.8 cM on chromosome 9, with the most likely position being located at 97.5 cM in agreement with both years of data (Table 5). A significant QTL was not found at this chromosomal location for yield.

TABLE 5

QTL positions and confidence intervals

| | | Major Peak (and 99% CI) in cM | |
|---|---|---|---|
| Trait | Year | QTL 9-1 | QTL 9-2 |
| Moisture | 2009 | 75.8 (71.7-76.7) | 97.5 (93.4-97.8) |
| Yield | 2009 | 75.8 (71.8-76.2) | — |
| Moisture | 2010 | 77.3 (76.3-78.7) | 97.5 (94.2-97.8) |
| Yield | 2010 | 76.2 (74.6-79.0) | — |

The spatial mixed linear base model with the addition of the two most likely QTL positions and an interaction between the positions was separately fit for the two years of data to assess the effect of these QTL positions for grain moisture and yield. Best linear unbiased predictions (BLUPs) were predicted from this model for all combinations of QTL 9-1 and QTL 9-2. At QTL 9-1, the PHCA5 alleles consistently resulted in an average decrease in kernel moisture across both years of testing when controlling for QTL 9-2 in the 93-98 cM region (Tables 6 and 7). There was also an associated decrease in yield within the same region (Tables 6 and 7). The effects at QTL 9-2, when controlling for QTL 9-1, showed that for this QTL the PH705 alleles decreased moisture levels but had no statistically significant effect on yield (Tables 6 and 7).

The greatest reduction in moisture can therefore be achieved through selection of the PHCA5 (designated as "B") alleles at QTL 9-1 and PH705 (designated as "A") alleles at QTL 9-2 (Tables 6 and 7). The QTL 9-1 region from 72-79 cM on a single meiosis map approximately corresponds with the region 200.4-230.6 cM on the IBM2 2008 map, and the QTL 9-2 region from 93-98 cM on a single meiosis map approximately corresponds with 317-323 cM on the IBM2 2008 map.

TABLE 6

Phenotypic BLUPs for moisture and yield based on allelic combinations at the two QTL detected in 2009 and 2010. AA = PH705 homozygous alleles and BB = PHCA5 homozygous alleles. QTL positions are as shown in Table 5.

| | | | Moisture | | Yield | |
|---|---|---|---|---|---|---|
| Year | QTL 9-1 | QTL 9-2 | Predicted Value | Standard Error | Predicted Value | Standard Error |
| 2009 | BB | BB | 25.35 | 0.19 | 208.33 | 1.93 |
| | BB | AA | 24.97 | 0.19 | 207.81 | 1.94 |
| | AA | BB | 26.05 | 0.19 | 214.16 | 1.93 |
| | AA | AA | 25.80 | 0.19 | 213.48 | 1.96 |
| 2010 | BB | BB | 21.25 | 0.16 | 201.64 | 2.08 |
| | BB | AA | 21.08 | 0.16 | 201.64 | 2.08 |
| | AA | BB | 21.99 | 0.16 | 207.91 | 2.09 |
| | AA | AA | 21.82 | 0.16 | 207.91 | 2.09 |

TABLE 7

Average difference in phenotype BLUPs due to PH705 alleles at each QTL, while controlling for alleles at the alternate QTL. QTL positions are as shown in Table 5.

| | | QTL 9-1 | | QTL 9-2 | |
|---|---|---|---|---|---|
| Region | Trait | Average difference (PH705-PHCA5) | Standard error | Average difference (PH705-PHCA5) | Standard error |
| 2009 | Moisture | 0.77 | 0.05 | −0.32 | 0.06 |
| | Yield | 5.75 | 0.52 | −0.60* | 0.43 |
| 2010 | Moisture | 0.74 | 0.04 | −0.17 | 0.04 |
| | Yield | 6.27 | 0.58 | 0* | 7.66E−04 |

*no significant effect

Example 2

Identification of Chromosome 9 Haolotypes for Marker Assisted Selection of Grain Moisture To identify favorable haplotypes associated with reduced grain moisture, PHCA5 and PH705 were compared to a group of 491 Stiff Stalk Synthetic inbreds, including Pioneer elite inbreds and key founder and public lines, based on SNP alleles in the regions of the moisture QTL. A set of 9 SNPs were identified that could be used for selection of the favorable QTL allele for moisture in PHCA5 between 73 and 78 cM and that showed consistent allelic inheritance across pedigrees (Table 8). A set of 7 SNPs were identified that could be used for selection of the favorable QTL allele for moisture at PH705 between 93 and 98 cM and that showed consistent allelic inheritance across pedigrees (Table 9).

TABLE 8

Markers that define a haplotype that differentiates PHCA5 from other inbreds in the region between 73 and 78 cM (based on single meiosis map, e.g. the PHB map) on chromosome 9.

| Marker | Reference Sequence | Primer Sequences | SNP Identifier | SNP Position in Reference Sequence | PHB Map Position | IBM2 Map Position | PHCA5 Allele |
|---|---|---|---|---|---|---|---|
| PHM229 | SEQ ID NO: 4 | SEQ ID NOs: 33-36 | PHM229-15 | 168 | 74.0 | 220.1 | C |
| PHM6567 | SEQ ID NO: 2 | SEQ ID NQs: 25-28 | PHM6567-10 | 246 | 75.2 | 220.7 | T |
| PHM9929 | SEQ ID NO: 5 | SEQ ID NOs: 37-40 | PHM9929-8 | 163 | 75.8 | 226.3 | T |
| PHM5208 | SEQ ID NO: 8 | SEQ ID NOs: 49-52 | PHM5208-11 | 413 | 75.9 | 226.3 | T |
| PHM15758 | SEQ ID NO: 7 | SEQ ID NOs: 45-48 | PHM15758-6 | 277 | 76.1 | 226.3 | C |
| PHM6667 | SEQ ID NO: 9 | SEQ ID NOs: 53-56 | PHM6667-11 | 237 | 76.2 | 226.3 | T |
| PHM14370 | SEQ ID NO: 11 | SEQ ID NOs: 61-64 | PHM14370-9 | 461 | 76.9 | 226.3 | G |
| PHM3159 | SEQ ID NO: 6 | SEQ ID NOs: 41-44 | PHM3159-14 | 217 | 77.0 | 226.3 | C |
| PHM17246 | SEQ ID NO: 10 | SEQ ID NOs: 57-60 | PHM17246-16 | 240 | 77.0 | 226.3 | T |

TABLE 9

Markers that define a haplotype that differentiates PH705 from other inbreds in the region between 93 and 98 cM (based on a single meiosis map, e.g. the PHB map) on chromosome 9.

| Marker | Reference Sequence | Primer Sequences | SNP Identifier | SNP Position in Reference Sequence | PHB Map Position | IBM2 Map Position | PH705 |
|---|---|---|---|---|---|---|---|
| PHM18292 | SEQ ID NO: 16 | SEQ ID NOs: 81-84 | PHM18292-9 | 285 | 94.4 | 317 | A |
| PHM4598 | SEQ ID NO: 14 | SEQ ID NOs: 73-76 | PHM4598-22 | 246 | 94.5 | N/A | C |
| PHM3507 | SEQ ID NO: 15 | SEQ ID NOs: 77-80 | PHM3507-13 | 454 | 94.6 | 317 | G |
| PHM3004 | SEQ ID NO: 17 | SEQ ID NOs: 85-88 | PHM3004-13 | 320 | 94.7 | 317 | G |
| PHM14122 | SEQ ID NO: 18 | SEQ ID NOs: 89-92 | PHM14122-22 | 166 | 97.0 | 320.6 | G |
| PHM10270 | SEQ ID NO: 19 | SEQ ID NOs: 93-96 | PHM10270-13 | 260 | 97.5 | 322.6 | C |
| PHM14092 | SEQ ID NO: 20 | SEQ ID NOs: 97-100 | PHM14092-77 | 253 | 97.8 | 322.6 | C |

These SNP alleles, alone or in combination, can be used to select for reduced moisture in maize Stiff Stalk Synthetic populations. The reference sequences for the PHM markers shown in Tables 8 and 9 are represented by SEQ ID NOs:1-20, and the primers for the PHM markers shown in Tables 8 and 9 are represented by SEQ ID NOs:21-100.

Example 3

Association Analysis

An association mapping strategy was undertaken to identify markers associated with MST (grain moisture) in maize. The association analysis utilized SNP genotype data that was directly obtained from maize inbreds and breeding value scores for grain moisture that were obtained through the analysis of testcrosses of the inbreds with multiple testers.

A structure-based association analysis was conducted using standard association mapping methods, where the population structure is controlled using marker data. The model-based cluster analysis software, Structure, developed by Pritchard et al., (Genetics 155:945-959 (2000)) was used with haplotype data to estimate admixture coefficients and assign the inbreds to subpopulations. The structure analysis resulted in five subpopulations. Kuiper's statistic for testing whether two distributions are the same was then used to test a given marker for association between haplotype and phenotype in a given subpopulation (Press et al., Numerical Recipes in C, second edition, Cambridge University Press, NY (2002)).

Two peaks of significant marker-trait associations (FIG. 2) on chromosome 9, identified in a stiff stalk subpopulation, overlapped with the QTL 9-1 and QTL 9-2 intervals described in EXAMPLE 1. Markers in the region of chromosome 9 from 74 to 79 cM (based on a single meiosis map) having the most significant associations with grain moisture were PHM229-15, PHM6567-10, and PHM4691-9. For the second region (QTL 9-2), markers PHM3507-13 and PHM3004-13 had the most significant associations with the grain moisture phenotype.

Table 10 provides a listing of the top chromosome 9 markers significantly associated with the mechanical stalk strength phenotype based on association analysis. A reduction in moisture was associated with a "1" at PHM4691-9, a "T" at PHM6567-10, and a "C" at PHM229-15 in the QTL 9-1 region and an "A" at PHM3507-13 and a "G" at PHM3004-13 in the QTL 9-2 region. The SEQ ID NO: for each marker reference sequence is shown in Table 10. Primers for these marker sequences are represented by SEQ ID NOs:33-36 (PHM229), 25-28 (PHM6567), 29-32 (PHM4691), 77-80 (PHM3507), and 85-88 (PHM3004).

TABLE 10

Markers associated with grain moisture in a stiff stalk population (identified using association analysis)

| Marker | Reference Sequence | SNP Identifier | P-value | Chr. 9 Position |
|---|---|---|---|---|
| PHM229 | SEQ ID NO: 4 | PHM229-15 | 6.579E−25 | 74.0 |
| PHM6567 | SEQ ID NO: 2 | PHM6567-10 | 2.661E−27 | 75.2 |
| PHM4691 | SEQ ID NO: 3 | PHM4691-9 | 1.19E−24 | 75.3 |
| PHM3507 | SEQ ID NO: 15 | PHM3507-13 | 1.358E−22 | 94.6 |
| PHM3004 | SEQ ID NO: 17 | PHM3004-13 | 1.623E−30 | 94.7 |

Example 4

Marker Assisted Selection at QTL9-1

The introgression of the reduced grain moisture QTL alleles can be achieved via repeated backcrossing to a recurrent parent accompanied by marker assisted selection to retain the alleles of the donor parent. This backcross procedure can be implemented at any stage in line development and can occur in conjunction with breeding for superior agronomic characteristics of one or more traits of interest, including transgenic and non-transgenic traits.

$BC_2$-$F_3$ (backcross) populations were created by backcrossing the QTL9-1 region from PHWRW (donor parent; has PHCA5 alleles) into PH134R, PHR1J, and PHCPR (RP=recurrent parents; do not have PHCA5 alleles). The markers used to genotype the region containing QTL9-1 were PHM14165-17, PHM15960-14, PHM5208-11 (see Table 8), PHM8438-6, PHM9867-22, and PHM14523-8 (See Table 11 for marker information). The BC2 lines were selfed twice and markers were used to select lines homozygous for the QTL9-1 PHWRW haplotype and lines homozygous for the PH134R, PHR1J, and PHCPR haplotypes.

These lines were topcrossed to the tester PH1C1S1 to create hybrid seed for evaluation.

The effect of the QTL9-1 haplotype was evaluated by comparing grain moisture and yield of the topcrossed $BC_2$-$F_3$ lines with the QTL to the lines without the QTL in a hybrid yield experiment. The hybrid entries were planted in five locations, and BLUPS data from a spatial linear mixed model of moisture and yield was analyzed. The hybrid data for grain moisture and yield is shown in Table 12. The donor parent or recurrent parent genotype of the entries was determined using PHM5208-11. The p-value shown is the p-value of the difference between the haplotypes with respect to either yield (YLD) or grain moisture (MST).

TABLE 11

Markers used to Genotype the Region Containing QTL9-1

| Marker | Reference Sequence | Primer Sequences | SNP Identifier | SNP Position in Reference Sequence | Chr. 9 Position (single meiosis map) |
|---|---|---|---|---|---|
| PHM14165 | SEQ ID NO: 156 | SEQ ID NOs: 161-164 | PHM14165-17 | 432 | 72.5 |
| PHM15960 | SEQ ID NO: 157 | SEQ ID NOs: 165-168 | PHM15960-14 | 246 | 73.02 |
| PHM8438 | SEQ ID NO: 158 | SEQ ID NOs: 169-172 | PHM8438-6 | 427 | 78.56 |
| PHM9867 | SEQ ID NO: 159 | SEQ ID NOs: 173-176 | PHM9867-22 | 355 | 80.29 |
| PHM14523 | SEQ ID NO: 160 | SEQ ID NOs: 177-180 | PHM14523-8 | 342 | 85 |

TABLE 12

Yield and Moisture Phenotypic analysis of Topcross experiments.

| Variable | N | Mean | SE Mean | StDev | Difference | T-Test of Difference (P-vaue) |
|---|---|---|---|---|---|---|
| YLD-PH134R-RP | 23 | 187.95 | 0.73 | 3.50 | | |
| YLD-PH134R-DP | 30 | 186.81 | 0.50 | 2.73 | 1.14 | 0.205 |
| YLD-PHR1J-RP | 30 | 188.89 | 0.65 | 3.55 | | |
| YLD-PHR1J-DP | 20 | 188.45 | 0.64 | 2.87 | 0.44 | 0.633 |
| YLD-PHCPR-RP | 26 | 173.82 | 0.75 | 3.84 | | |
| YLD-PHCPR-DP | 50 | 172.21 | 0.46 | 3.24 | 1.61 | 0.074 |
| MST-PH134R-RP | 23 | 25.14 | 0.20 | 0.94 | | |
| MST-PH134R-DP | 30 | 23.88 | 0.15 | 0.83 | 1.26 | 0.000 |
| MST-PHR1J-RP | 30 | 26.19 | 0.16 | 0.89 | | |
| MST-PHR1J-DP | 20 | 25.42 | 0.17 | 0.74 | 0.77 | 0.000 |
| MST-PHCPR-RP | 26 | 21.43 | 0.13 | 0.66 | | |
| MST-PHCPR-DP | 50 | 20.61 | 0.09 | 0.63 | 0.82 | 0.000 |

Lines having the PHWRW haplotype have grain moisture averages of 0.77-1.26 less than the grain moisture averages of lines not having the PHWRW haplotype but also show decreases in yield. The differences between the haplotypes with respect to grain moisture were statistically significant; however, the differences between the haplotypes with respect to grain yield were not significant. Thus, by selecting for the favorable alleles at QTL9-1 using marker assisted selection, grain moisture was significantly less in the lines that did not have the favorable alleles.

What is claimed:

1. A method of producing a maize plant with reduced grain moisture, the method comprising:
   a. obtaining a sample of nucleic acids from maize germplasm;
   b. detecting in said sample at least one marker allele located within
      a chromosomal interval defined by and including PHM18206 and PHM4910, wherein the at least one marker allele is associated with a haplotype comprising a "T" at PHM9929-8, a "T" at PHM6667-11, a "C" at PHM229-15, a "T" at PHM6567-10, a "T" at PHM5208-11, a "C" at PHM15758-6, a "G" at PHM14370-9, a "C" at PHM3159-14, and a "T" at PHM17246-16;
   c. selecting said maize germplasm that has the at least one marker allele that is associated with the haplotype comprising a "T" at PHM9929-8, a "T" at PHM6667-11, a "C" at PHM229-15, a "T" at PHM6567-10, a "T" at PHM5208-11, a "C" at PHM15758-6, a "G" at PHM14370-9, a "C" at PHM3159-14, and a "T" at PHM17246-16;
   d. crossing said maize germplasm comprising said at least one marker allele with a second maize plant;
   e. obtaining progeny seeds from said cross; and
   f. growing at least one maize plant from said progeny seeds,
   wherein said maize plant grown from said progeny seeds comprises said at least one marker allele and has reduced grain moisture when compared with a maize plant which does not comprise said at least one marker allele;
   further wherein the maize plant is a Stiff Stalk Synthetic inbred or a progeny plant derived therefrom.

2. A method of producing a maize plant with reduced grain moisture, the method comprising:
   a. obtaining a sample of nucleic acids from maize germplasm;
   b. detecting in said sample a haplotype comprising a "T" at PHM9929-8, a "T" at PHM6667-11, a "C" at PHM229-15, a "T" at PHM6567-10, a "T" at PHM5208-11, a "C" at PHM15758-6, a "G" at PHM14370-9, a "C" at PHM3159-14, and a "T" at PHM17246-16;
   c. selecting said maize germplasm that has the haplotype;
   d. crossing said maize germplasm from (c) with a second maize plant;
   e. obtaining progeny seeds from said cross; and
   f. growing at least one maize plant from said progeny seeds,
   wherein said maize plant grown from said progeny seeds comprises the haplotype and has reduced grain moisture when compared with a maize plant which does not comprise the haplotype;
   further wherein the maize plant is a Stiff Stalk Synthetic inbred or a progeny plant derived therefrom.

* * * * *